(12) United States Patent
Efimov et al.

(10) Patent No.: US 12,344,826 B2
(45) Date of Patent: Jul. 1, 2025

(54) APPARATUS AND METHODS FOR IN VITRO PRECLINICAL HUMAN TRIALS

(71) Applicant: THE GEORGE WASHINGTON UNIVERSITY, A CONGRESSIONALLY CHARTERED NOT-FOR-PROFIT CORPORATION, Washington, DC (US)

(72) Inventors: Igor R. Efimov, Arlington, VA (US); Yun Qiao, Arlington, VA (US); Chaoyi Kang, Arlington, VA (US); Zhenyu Li, McLean, VA (US); Quan Dong, Fairfax, VA (US); Baichen Li, Falls Church, VA (US)

(73) Assignee: THE GEORGE WASHINGTON UNIVERSITY, A CONGRESSIONALLY CHARTERED NOT-FOR-PROFIT CORPORATION, Washington, DC (US)

( * ) Notice: Subject to any disclaimer, the term of this patent is extended or adjusted under 35 U.S.C. 154(b) by 1461 days.

(21) Appl. No.: 16/479,297

(22) PCT Filed: Jan. 24, 2018

(86) PCT No.: PCT/US2018/015052
§ 371 (c)(1),
(2) Date: Jul. 19, 2019

(87) PCT Pub. No.: WO2018/140497
PCT Pub. Date: Aug. 2, 2018

(65) Prior Publication Data
US 2019/0376014 A1 Dec. 12, 2019

Related U.S. Application Data

(60) Provisional application No. 62/450,412, filed on Jan. 25, 2017.

(51) Int. Cl.
*C12M 3/06* (2006.01)
*A01N 1/122* (2025.01)
(Continued)

(52) U.S. Cl.
CPC ............ *C12M 23/16* (2013.01); *A01N 1/122* (2025.01); *A01N 1/143* (2025.01); *A01N 1/16* (2025.01); *A01N 1/162* (2025.01); *B01L 3/502715* (2013.01); *C12M 27/02* (2013.01); *C12M 27/16* (2013.01); *C12M 29/10* (2013.01); *C12M 41/06* (2013.01); *C12M 41/18* (2013.01); *C12M 41/26* (2013.01); *C12M 41/34* (2013.01); *C12M 41/48* (2013.01); *C12N 5/0657* (2013.01); *C12N 5/0697* (2013.01); *C12N 9/22* (2013.01); *C12N 15/11* (2013.01); *G01N 1/36* (2013.01); *G01N 33/5014* (2013.01); *G01N 33/5088* (2013.01); *B01L 2200/025* (2013.01); *B01L 2200/10* (2013.01); *B01L 2200/143* (2013.01); *B01L 2200/185* (2013.01); *B01L 2300/027* (2013.01); *B01L 2300/0645* (2013.01); *B01L 2300/0663* (2013.01); *B01L 2300/0819* (2013.01); *B01L 2300/10* (2013.01); *B01L 2300/12* (2013.01); *B01L 2300/18* (2013.01);
(Continued)

(58) Field of Classification Search
CPC .... A01N 1/021; A01N 1/0247; A01N 1/0278; A01N 1/0284; B01L 2200/025; B01L 2200/10; B01L 2200/143; B01L 2200/185; B01L 2300/027; B01L 2300/0645; B01L 2300/0663; B01L 2300/0819; B01L 2300/10; B01L 2300/12; B01L 2300/18; B01L 2400/0415; B01L 2400/0487; B01L 3/502715; C12M 23/16; C12M 27/02; C12M 27/16; C12M 29/10; C12M 41/06; C12M 41/18; C12M 41/26; C12M 41/34; C12M 41/48; C12M 21/00; C12M 41/00; C12N 15/11; C12N 2310/20; C12N 2521/00; C12N 2800/80; C12N 5/0657; C12N 5/0697; C12N 9/22; G01N 1/36; G01N 2001/368; G01N 33/48707; G01N 33/5014; G01N 33/5088
See application file for complete search history.

(56) References Cited

U.S. PATENT DOCUMENTS 3,948,732 A 4/1976 Haddad et al.
5,693,537 A 12/1997 Wilson et al.
(Continued)

FOREIGN PATENT DOCUMENTS

WO WO-2014089290 A1 6/2014
WO WO-2015192038 A1 12/2015
(Continued)

OTHER PUBLICATIONS

Brandenburger et al. Cardiovascular Research (2012) 93, 50-59. (Year: 2012).*
(Continued)

*Primary Examiner* — Jeremy C Flinders
*Assistant Examiner* — Masudur Rahman
(74) *Attorney, Agent, or Firm* — Sterne, Kessler Goldstein & Fox P.L.L.C.

(57) ABSTRACT

Systems comprising a microfluidic device are provided for maintaining and analyzing tissue slices. Methods for maintaining tissue slices in a microfluidic device are further provided.

14 Claims, 23 Drawing Sheets

(51) Int. Cl.

| | |
|---|---|
| *A01N 1/143* | (2025.01) |
| *A01N 1/16* | (2025.01) |
| *A01N 1/162* | (2025.01) |
| *B01L 3/00* | (2006.01) |
| *C12M 1/00* | (2006.01) |
| *C12M 1/02* | (2006.01) |
| *C12M 1/06* | (2006.01) |
| *C12M 1/34* | (2006.01) |
| *C12M 1/36* | (2006.01) |
| *C12N 5/071* | (2010.01) |
| *C12N 5/077* | (2010.01) |
| *C12N 9/22* | (2006.01) |
| *C12N 15/11* | (2006.01) |
| *G01N 1/36* | (2006.01) |
| *G01N 33/50* | (2006.01) |

(52) U.S. Cl.
CPC ............... *B01L 2400/0415* (2013.01); *B01L 2400/0487* (2013.01); *C12N 2310/20* (2017.05); *C12N 2800/80* (2013.01); *G01N 2001/368* (2013.01)

(56) References Cited

U.S. PATENT DOCUMENTS

| | | | | |
|---|---|---|---|---|
| 7,855,070 | B2* | 12/2010 | Vukasinovic | C12M 35/02 |
| | | | | 435/293.1 |
| 8,440,431 | B2 | 5/2013 | Voytas et al. | |
| 8,440,432 | B2 | 5/2013 | Voytas et al. | |
| 8,450,471 | B2 | 5/2013 | Voytas et al. | |
| 2006/0249875 | A1 | 11/2006 | Robb et al. | |
| 2009/0075360 | A1* | 3/2009 | Ho | C12M 41/48 |
| | | | | 435/284.1 |
| 2011/0050041 | A1* | 3/2011 | Yamamoto | F03G 7/005 |
| | | | | 310/338 |
| 2012/0100602 | A1 | 4/2012 | Lu et al. | |
| 2014/0256798 | A1 | 9/2014 | Osborn | |

FOREIGN PATENT DOCUMENTS

| | | |
|---|---|---|
| WO | WO-2016036532 A1 | 3/2016 |
| WO | WO-2016125143 A1 | 8/2016 |
| WO | WO-2016178207 A1 | 11/2016 |

OTHER PUBLICATIONS

Kang et al. Sci Rep. 2016; 6: 28798. (Year: 2016).*
Barclay, C.J., "Modelling diffusive O(2) supply to isolated preparations of mammalian skeletal and cardiac muscle," J Muscle Res Cell Motil, Springer Nature, Germany 26(4-5):225-235 (2005).
Berger, H.J., et al., "Continual electric field stimulation preserves contractile function of adult ventricular myocytes in primary culture," Am J Physiol 266(1 Pt 2):H341-H349, American Physiological Society, United States (Jan. 1994).
Bird, S.D., et al., "The human adult cardiomyocyte phenotype," Cardiovasc Res 58(2):423-434, Elsevier, Netherlands (May 2003).
Brandenburger, M., et al., "Organotypic slice culture from human adult ventricular myocardium," Cardiovasc Res 93(1):50-59, Oxford University Press, United Kingdom (Jan. 2012).
Bussek, A., et al., "Cardiac tissue slices with prolonged survival for in vitro drug safety screening," J Pharmacol Toxicol Methods 66(2):145-151, Elsevier, Netherlands (Sep. 2012).
Camelliti, P., et al., "Adult human heart slices are a multicellular system suitable for electrophysiological and pharmacological studies," J Mol Cell Cardiol 51(3):390-398, Elsevier, Netherlands (Sep. 2011).
Chi, K.R., "Revolution dawning in cardiotoxicity testing," Nat Rev Drug Discov 12(8):565-567, Springer Nature, Germany (Aug. 2013).

Choate, J.K., and Feldman, R., "Neuronal control of heart rate in isolated mouse atria," Am J Physiol Heart Circ Physiol 285(3):H1340-H1346, American Physiological Society, United States (Sep. 2003).
Coppini, R., et al., "Isolation and functional characterization of human ventricular cardiomyocytes from fresh surgical samples," J Vis Exp (86):51116, MyJoVE Corporation, United States (Apr. 2014).
Dmitriev, I., "An adenovirus vector with genetically modified fibers demonstrates expanded tropism via utilization of a coxsackievirus and adenovirus receptor-independent cell entry mechanism," J Virol 72(12):9706-9713, American Society for Microbiology, United States (Dec. 1998).
Dumaine, R., et al., "Ionic mechanisms responsible for the electrocardiogramotype of the Brugada syndrome are temperature dependent," Circ Res 85(9):803-809, American Heart Association, United States (Oct. 1999).
Esch, M.B., et al., "Modular, pumpless body-on-a-chip platform for the co-culture of GI tract epithelium and 3D primary liver tissue," Lab Chip 16(14):2719-2729, Royal Society of Chemistry, United Kingdom (Jul. 2016).
FANTOM Consortium and the RIKEN PMI and CLST (DGT), "A promoter-level mammalian expression atlas," Nature 507(7493):462-470, Springer Nature, Germany (Mar. 2014).
Folliguet, T.A., et al., "Adult cardiac myocytes survive and remain excitable during long-term culture on synthetic supports," J Thorac Cardiovasc Surg 121(3):510-519, Elsevier, Netherlands (Mar. 2001).
Giordano, F.J., "Oxygen, oxidative stress, hypoxia, and heart failure," J Clin Invest 115(3):500-508, American Society for Clinical Investigation, United States (Mar. 2005).
Glukhov, A.V., et al., "Differential K(ATP) channel pharmacology in intact mouse heart," J Mol Cell Cardiol 48(1):152-160, Elsevier, Netherlands (Jan. 2010).
Glukhov, A.V., et al., "Transmural dispersion of repolarization in failing and nonfailing human ventricle," Circ Res 106(5):981-991, Lippincott Williams & Wilkins, United States (Mar. 2010).
Glukhov, A.V., et al., "Conduction remodeling in human end-stage nonischemic left ventricular cardiomyopathy," Circulation 125(15):1835-1847, Lippincott Williams & Wilkins, United States (Apr. 2012).
Govorunova, E.G., et al., "Natural light-gated anion channels: A family of microbial rhodopsins for advanced optogenetics," Science 349(6248):647-650, American Association for the Advancement of Science, United States (Aug. 2015).
Hasenfuss, G., "Animal models of human cardiovascular disease, heart failure and hypertrophy," Cardiovasc Res 39(1):60-76, Oxford University Press, United Kingdom (Jul. 1998).
Hong, J., et al., "Cardiac RNAi therapy using RAGE siRNA/ deoxycholic acid-modified polyethylenimine complexes for myocardial infarction," Biomaterials 35(26):7562-7573, Elsevier, Netherlands (Aug. 2014).
Huang, Y., et al., "Cardiac myocyte-specific HIF-1alpha deletion alters vascularization, energy availability, calcium flux, and contractility in the normoxic heart," FASEB J 18(10):1138-1140, Federation of American Societies for Experimental Biology, United States (Jul. 2004).
International Search Report and Written Opinion for International Application No. PCT/US2018/015052, International Search Authority, United States, mailed on Apr. 4, 2018, 22 pages.
Itzhaki, I., et al., "Modelling the long QT syndrome with induced pluripotent stem cells," Nature 471(7337):225-229, Springer Nature, Germany (Mar. 2011).
Jia, Z., et al., "Stimulating cardiac muscle by light: cardiac optogenetics by cell delivery," Circ Arrhythm Electrophysiol 4(5):753-760, Lippincott Williams & Wilkins, United States (Oct. 2011).
Kaneko, M. et al., "Histological Validation of Heart Slices as a Model in Cardiac Research," J Cell Sci Ther 3(4):e1000126, Longdom Publishing, Belgium (2012).
Kang, C., et al., "Human Organotypic Cultured Cardiac Slices: New Platform For High Throughput Preclinical Human Trials," Sci Rep 6:28798, Springer Nature, Germany (Jun. 2016).
Karakikes, I., et al., "Human induced pluripotent stem cell-derived cardiomyocytes: insights into molecular, cellular, and functional phenotypes," Circ Res 117(1):80-88, Lippincott Williams & Wilkins, United States (Jun. 2015).

(56) References Cited

OTHER PUBLICATIONS

Laughner, J.I., "Processing and analysis of cardiac optical mapping data obtained with potentiometric dyes," Am J Physiol Heart Circ Physiol 303(7):H753-H765, American Physiological Society, United States (Oct. 2012).
Loskill, P., et al., "WAT-on-a-chip: a physiologically relevant microfluidic system incorporating white adipose tissue," Lab Chip 17(9):1645-1654, Royal Society of Chemistry, United Kingdom (May 2017).
Lou, Q., et al., "Transmural heterogeneity and remodeling of ventricular excitation-contraction coupling in human heart failure," Circulation 123(17):1881-1890, Lippincott Williams & Wilkins, United States (May 2011).
Lou, Q., et al., "Multiparametric optical mapping of the Langendorff-perfused rabbit heart," J Vis Exp (55):3160, MyJoVE Corporation, United States (Sep. 2011).
Mak; I.W., et al., "Lost in translation: animal models and clinical trials in cancer treatment," Am J Transl Res 6(2):114-118, e-Century Publishing Corporation, United States (Jan. 2014).
McMurtrey, R.J., "Analytic Models of Oxygen and Nutrient Diffusion, Metabolism Dynamics, and Architecture Optimization in Three-Dimensional Tissue Constructs with Applications and Insights in Cerebral Organoids," Tissue Eng Part C Methods 22(3):221-249, Mary Ann Liebert, United States (Mar. 2016).
Milburn, T., et al., "The temperature dependence of conductance of the sodium channel: implications for mechanisms of ion permeation," Recept Channels 3(3):201-211, Taylor & Francis Group, United Kingdom (1995).
Moreno, A., "Enzyme-dependent fluorescence recovery of NADH after photobleaching to assess dehydrogenase activity of isolated perfused hearts," Sci Rep 7:45744, Springer Nature, Germany (Mar. 2017).
Nerbonne, J.M., et al., "Genetic manipulation of cardiac K(+) channel function in mice: what have we learned, and where do we go from here?" Circ Res 89(11):944-956, Lippincott Williams & Wilkins, United States (Nov. 2001).
Phan, D.T.T., et al., "A vascularized and perfused organ-on-a-chip platform for large-scale drug screening applications," Lab Chip 17(3):511-520, Royal Society of Chemistry, United Kingdom (Jan. 2017).
Poller, W., et al., "Cardiac-targeted delivery of regulatory RNA molecules and genes for the treatment of heart failure," Cardiovasc Res 86(3):353-364, Oxford University Press, United Kingdom (Jun. 2010).
Radisic, M., et al., "Functional assembly of engineered myocardium by electrical stimulation of cardiac myocytes cultured on scaffolds," Proc Natl Acad Sci USA 101(52):18129-18134, National Academy of Science, United States (Dec. 2004).
Robertson, C., et al., "Concise review: maturation phases of human pluripotent stem cell-derived cardiomyocytes," Stem Cells 31(5):829-837, Oxford University Press, United Kingdom (May 2013).
Sander, J.D., and Joung, J.K., "CRISPR-Cas systems for editing, regulating and targeting genomes," Nat Biotechnol 32(4):347-355, Springer Nature, Germany (Apr. 2014).
Somasuntharam, I., et al., "Delivery of Nox2-NADPH oxidase siRNA with polyketal nanoparticles for improving cardiac function following myocardial infarction," Biomaterials 34(31):7790-7798, Elsevier, Netherlands (Oct. 2013).
Suckau, L., "Long-term cardiac-targeted RNA interference for the treatment of heart failure restores cardiac function and reduces pathological hypertrophy," Circulation 119(9):1241-1252, Lippincott Williams & Wilkins, United States (Mar. 2009).
Swaminathan, P.D., et al., "Oxidized CaMKII causes cardiac sinus node dysfunction in mice," J Clin Invest 121(8):3277-3288, American Society for Clinical Investigation, United States (Aug. 2011).
Thomas, C.E., et al., "Progress and problems with the use of viral vectors for gene therapy," Nat Rev Genet 4(5):346-358, Springer Nature, Germany (May 2003).
Voets, T., et al., "The principle of temperature-dependent gating in cold- and heat-sensitive TRP channels," Nature 430(7001):748-754, Springer Nature, Germany (Aug. 2004).
Wetmur, J.G., and Davidson, N., "Kinetics of renaturation of DNA," J Mol Biol 31(3):349-370, Elsevier, Netherlands (Feb. 1968).

\* cited by examiner

Day 0

Day 21

APPARATUS AND METHODS FOR IN VITRO PRECLINICAL HUMAN TRIALS

CROSS-REFERENCE TO RELATED APPLICATIONS

This application claims the benefit of U.S. Provisional Application No. 62/450,412, filed Jan. 25, 2017, which is incorporated herein by reference in its entirety.

STATEMENT REGARDING FEDERALLY-SPONSORED RESEARCH AND DEVELOPMENT

"This invention was made with U.S. Government support under grants R01 HL114395 and R01 HL126802 from the National Heart, Lung and Blood Institute of National Institutes of Health. "The U.S. Government has certain rights in this invention.

FIELD OF THE INVENTION

The present subject matter relates, in general, to novel platforms and methods for the investigation of normal and pathological physiology, including human cardiac physiology, in vitro and the long-term organotypic culture of tissue, including human cardiac tissue, for in vitro pre-clinical testing.

BACKGROUND OF THE INVENTION

Physiologically and genetically accurate models of the human heart are indispensable for studying human cardiac physiology and for pre-clinical screening of candidate biological and drug therapies for their efficacy and/or toxicity. However, pre-clinical screening has been mostly limited to animal models and/or cell lines, which do not fully recapitulate human biology. Few studies have demonstrated long-term functional recordings from the human heart due to difficulties in obtaining and maintaining electrically viable tissue samples, and lack of reliable model systems of the human myocardium.

Although crucial for fundamental biological discovery, animal models often fail to predict human response to treatments due to inter-species genetic and physiological differences (Hasenfuss, G., Cardiovasc. Res. 39(1):60-76 (1998); Mak, I. W. Y. et al., Am. J. Transl. Res. 6(2):114-8 (2014); Nerbonne, J. M. et al., Circ. Res. 89(11):944-56 (2001); FANTOM Consortium and the RIKEN PMI and CLST (DGT) et al., Nature 507,462-70 (2014), each of which is incorporated herein by reference in its entirety). In recent years, vibratome-cut human cardiac slices from donor and end-stage failing hearts have emerged as a promising model of the human heart for electrophysiological and pharmacological studies (Brandenburger, M. et al., Cardiovasc. Res. 93(1):50-9 (2012); Camelliti, P. et al., J. Mol. Cell. Cardiol. 51(3), 390-8 (2011), each of which is incorporated herein by reference in its entirety). It has been demonstrated that human cardiac slices faithfully recapitulate tissue level human cardiac physiology, exhibiting normal conduction velocity (CV), action potential duration (APD), intracellular calcium dynamics, heart rate dependence of these parameters and their response to α- and β-adrenergic stimulation (Kang, C. et al., Sci. Rep. 6:28798 (2016), which is incorporated herein by reference in its entirety). However, previous studies have only achieved short-term organotypic culture of human cardiac slices.

Extensive efforts have been invested into developing an authentic model of the human heart. Human induced pluripotent stem cell derived cardiomyocytes (hiPSC-CMs) are widely used in modeling diseases and drug screening (Chi, K. R., Nat. Rev. Drug Discov. 12(8):565-7 (2013); Itzhaki, I. et al., Nature 471(7337):225-9 (2011), each of which is incorporated herein by reference in its entirety). However, the development of hiPSC-CMs with mature atrial or ventricular phenotype has been challenging so far (Karakikes, I. et al., Circ. Res. 117(1):80-8 (2015); Robertson, C. et al., Stem Cells 31(5):829-37 (2013), each of which is incorporated herein by reference in its entirety).

Another approach to study human cardiac cell biology involved isolated primary human cardiomyocytes, which are functionally mature, but have limited experimental duration since they dedifferentiate in cell culture (Bird, S. D. et al., Cardiovasc. Res. 58(2):423-34 (2003); Coppini, R. et al., J. Vis. Exp. 86:e51116 (2014), each of which is incorporated herein by reference in its entirety). Different cardiomyocyte subpopulations can be obtained by altering the cell isolation process. However, they exhibit altered electrophysiology, i.e. action potential morphology, due to the lack of cell-cell coupling and membrane protein alterations caused by the tissue digestion procedure. The cell isolation procedure is also time consuming and labor intensive, thus limiting the use of isolated cardiomyocytes to low-throughput testing.

Another approach is based on the human ventricular wedge preparations, which allow for studying CV, conduction heterogeneity, and arrhythmia susceptibility (Glukhov, A. V. et al., Circulation 125(15):1835-47 (2012); Glukhov, A. V. et al., Circ. Res. 106(5):981-91 (2010); Lou, Q. et al., Circulation 123(17):1881-90 (2011), each of which is incorporated herein by reference in its entirety). Due to the complexity and variability of the coronary system and the size constraint of the preparation, the ventricular wedge preparation is also severely limited in terms of throughput. Primary cells, cell lines, and tissue also have significantly different gene expression profiles, as reported by the functional annotation of the Functional Annotation of the Mammalian Genome 5 (FANTOM5) consortium (FANTOM Consortium and the RIKEN PMI and CLST (DGT) et al., Nature 507,462-70 (2014)).

Human cardiac slices faithfully replicate the organ-level adult cardiac physiology because they retain the normal tissue architecture, multiple cell type environment, and extracellular matrix. (Kang, C. et al., Sci. Rep. 6:28798 (2016)). Therefore, human cardiac slices are advantageous over other in vitro and ex vivo model systems of cardiac physiology. For example, when compared with hiPSC-CMs, human cardiac slices more faithfully replicate adult human cardiac electrophysiology with a mature myocyte phenotype, tissue structure and multicellular environment. When compared with isolated human myocytes, cardiac slices largely preserve the natural multicellular environment and coupling with the surrounding myocytes, helping to maintain the fully differentiated cellular and tissue phenotype. Maintenance of the native tissue context is especially important for testing human gene therapy approaches. When compared with human ventricular wedge preparations, cardiac slices do not require intact human ventricles and can be obtained from small biopsy samples. Most importantly, human cardiac slices can be prepared at a thickness around the diffusion limit of oxygen. At the diffusion limit for oxygen, human cardiac slices can be cultured long-term for studying chronic drug treatment, gene expression regulation, and genetic engineering (Barclay, C. J., J. Muscle Res. Cell Motil. 26(4-5):225-35 (2005); Brandenburger, M. et al., Cardiovasc. Res. 93(1):50-9 (2012); Bussek, A. et al., J. Pharmacol. Toxicol. Methods 66(2):145-51 (2012); Kang, C. et al., Sci. Rep. 6:28798 (2016), each of which is incorporated herein by reference in its entirety). However, there are significant drawbacks to previously disclosed studies utilizing human cardiac slices.

Previous studies on the organotypic culture of ventricular slices obtained from adult mammalian hearts have been limited to about two days, which diminishes the usefulness of the preparation for testing the effects of chronic drug and gene therapies (Brandenburger, M. et al., Cardiovasc. Res. 93(1):50-9 (2012); Bussek, A. et al., J. Pharmacol. Toxicol. Methods 66(2):145-51 (2012); Kang, C. et al., Sci. Rep. 6:28798 (2016)). Lacking pacemaking abilities, slices collected from the ventricles of the heart undergo significant dedifferentiation, when cultured with conventional tissue culture techniques that lack electrical or mechanical stimulation and loading (Brandenburger, M. et al., Cardiovasc. Res. 93(1):50-9 (2012); Kaneko, M. et al., J. Cell Sci. Ther. 3(4):e1000126 (2012), each of which is incorporated herein by reference in its entirety). Human tissue and primary cells have been implemented in body-on-a-chip systems designed for drug testing (Esch, M. B. et al., Lab Chip 16(14):2719-29 (2016); Loskill, P. et al., Lab Chip 17(9):1645-54 (2017); Phan, D. T. T. et al., Lab Chip 17(3):511-20 (2017), each of which is incorporated herein by reference in its entirety). However, due to difficulties in maintaining the mature phenotype of adult human cardiac tissue in vitro, thus far there has not been a heart-on-a-chip system that supports long term organotypic culture of the human cardiac tissue.

Thus, there remains an unmet need for systems and methods for achieving long-term culture of tissue slices while maintaining a specific phenotype of the tissue slice, in particular for maintaining an adult cardiomyocyte phenotype in human cardiac slices. Disclosed herein are culture systems and methods of using the same for organotypic culture of tissue slices. In some preferred embodiments, the culture system is a human-heart-on-a-chip culture for organotypic culture of human cardiac tissue slices. The prolonged culture of tissue slices (e.g., human cardiac slices) demonstrated here allows for the study of chronic drug effects, gene therapies, and gene editing. To achieve long-term culture and to minimize tissue differentiation, the culture system is an automated system which supports media circulation, oxygenation, temperature control, electrical stimulation, and mechanical loading. The culture parameters can be individually adjusted to establish the optimal culture condition. The culture system is also entirely self-contained to allow for the transport of live cardiac slices to share for scientific research and drug testing.

BRIEF SUMMARY OF THE INVENTION

Human cardiac slices have emerged as a promising model of the human heart for scientific research and drug testing. Retaining the normal tissue architecture, multiple cell type environment, and the native extracellular matrix, human cardiac slices faithfully replicate the organ-level adult cardiac physiology without dedifferentiation.

As described herein, organotypic culture conditions have been optimized to maintain normal electrophysiology of the human cardiac slices long-term, and an automated, self-contained heart-on-a-chip system has been developed for maintaining tissue viability and for transporting live tissue. The prolonged culture of human cardiac slices described herein allows for the study of chronic drug effects, gene therapies, and gene editing. To achieve long-term culture and to minimize tissue dedifferentiation, the culture system described herein supports media circulation, oxygenation, temperature control, electrical stimulation, and mechanical loading. The culture parameters can be individually adjusted to establish the optimal culture condition. The heart-on-a-chip technology described herein further facilitates the use of organotypic human cardiac slices as a platform for pre-clinical drug testing and research in human cardiac physiology.

The present disclosure provides a system for maintaining and analyzing tissue slices, wherein the system comprises: a microfluidic device comprising at least one tissue culture chamber; one or more actuators disposed in an interior of the tissue culture chamber; one or more sensors disposed in the interior of the tissue culture chamber; and an electronics module comprising a microcontroller, wherein the electronics module is coupled to the one or more actuators and the one or more sensors by an array of electrodes.

The present disclosure further provides a method for maintaining one or more tissue slices in a microfluidic device, the method comprising culturing the one or more tissue slices in the microfluidic device, wherein the tissue slices are obtained from one or more organs, and wherein the microfluidic device comprises: a) one or more tissue culture chambers, wherein each tissue culture chamber provides a restricted environment supplied with oxygen and nutrients necessary to maintain a desired phenotype for each tissue slice; b) one or more actuators for maintenance of the one or more tissue slices or for phenotypic interrogation of the one or more tissue slices; c) one or more sensors for measuring one or more physiological parameters of the one or more tissue slices; and d) an electronics module comprising a microcontroller, wherein the electronics module is coupled to the one or more actuators and the one or more sensors by an array of electrodes.

Further objects and advantages of the present invention will be clear from the description that follows.

BRIEF DESCRIPTION OF THE DRAWINGS

FIG. 2 shows conduction velocity of culture human cardiac slices at 1,000 milliseconds (ms) pacing cycle length. The data are shown as mean±standard deviation. The statistical analysis was performed using one-way ANOVA followed by a Dunnett's multiple comparisons test.

FIG. 8 shows the recovery of murine sinus rhythm with medium circulation. FIG. 9 shows the recovery of murine sinus rhythm with medium oxygenation.

FIGS. 11-13 show that human cardiac slices remained viable for 21 days in culture. FIG. 11 shows the conduction velocity (cm/s) of cultured human cardiac slices over time. No significant changes in conduction velocity are observed in human cardiac slices cultured for two days and four days when compared with fresh human cardiac slices. The data are shown as mean±standard deviation. The statistical analysis was performed using one-way ANOVA followed by a Dunnett's multiple comparisons test. FIG. 12 shows a comparison of action potentials of a fresh human cardiac slice ("Day 0") and a human cardiac slice cultured for 21 days ("Day 21").

FIG. 16 illustrates example components of a culture system.

FIG. 19 illustrates a CNC milled gas exchanger. The top chamber is made of polycarbonate for liquid medium to pass through. The bottom chamber is made of stainless steel and is heated with a thermofoil heater. FIG. 20 depicts a 3D printed peristaltic pump. FIG. 21 depicts a portable gas tank and miniature pressure regulator. FIG. 22 shows recorded temperatures of the heater and the culture chamber. The culture chamber temperature rapidly reached and maintained physiological temperature with minimal fluctuation. FIG. 23 shows the dissolved oxygen level in culture medium with different gas. The oxygen concentration in the liquid medium rapidly reached saturation when the gas exchanger was filled with oxygen. The dissolved oxygen was depleted when the gas exchanger was filled with nitrogen.

FIGS. 24-27 relate to organotypic culture of human and murine cardiac tissue in a heart-on-a-chip culture system. FIG. 25 shows the action potential recorded from the slices using optical mapping. The heart-on-a-chip system maintained a stable heart rate of the cultured murine atrial preparation (FIG. 26). FIG. 27 shows the far-field recording of the cultured murine atrial preparation.

DETAILED DESCRIPTION OF ILLUSTRATIVE EMBODIMENTS

Figure 1A:
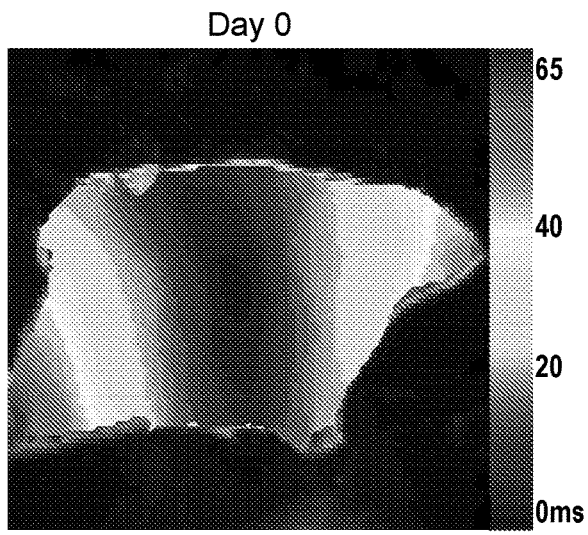
FIGS. 1 and 2 show that human cardiac slices remained viable for six days in culture, which allows for long-term pharmaceutical testing and evaluation of gene therapies. Human cardiac slices were cultured with 3 mL of medium in 6 well dishes placed on an orbital shaker at 20 rpm in a tri-gas incubator with 5% $CO_2$ and 30% $O_2$. The culture medium was comprised of Medium 199 (M4530, Sigma-Aldrich, St. Louis, MO), 1× Insulin-Transferrin-Selenium (ITS; I3146, Sigma-Aldrich, St. Louis, MO) liquid media supplement, 2% penicillin-streptomycin (P4333, Sigma-Aldrich, St. Louis, MO). Culture medium was replaced every two days. Activation maps were obtained from optical mapping experiments for conduction velocity calculations at day 0 (FIG. 1A), day 2 (FIG. 1B), day 3 (FIG. 1C), and day 4 (FIG. 1D) in culture.
Figure 1B:
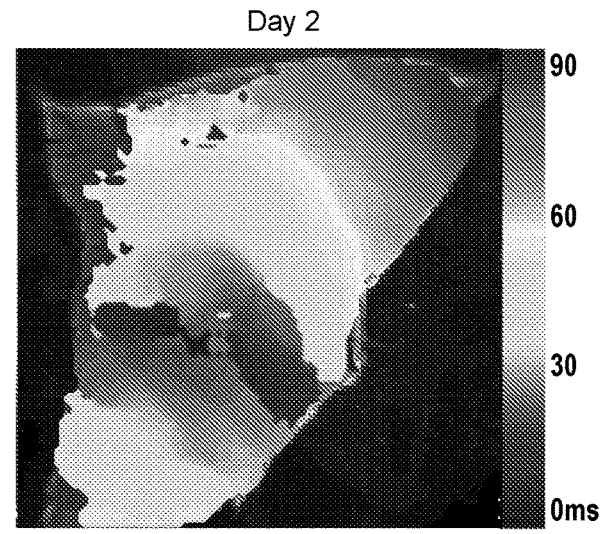
Figure 1C:
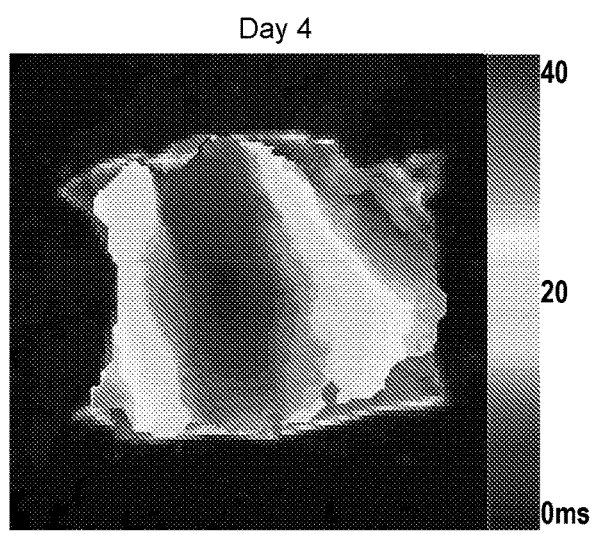
Figure 1D:
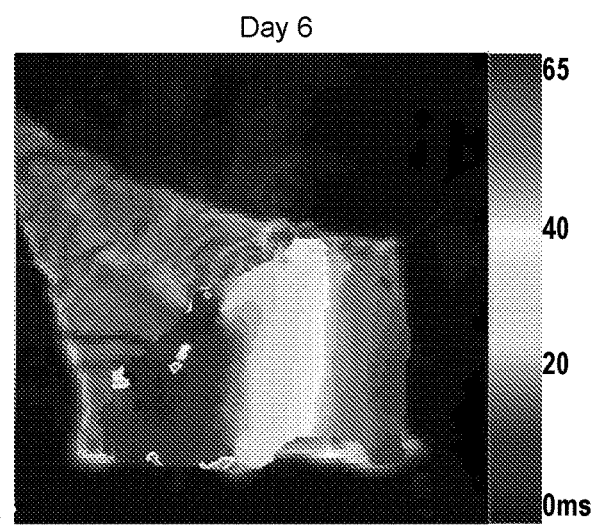

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

I. Definitions

Various terms relating to aspects of the description are used throughout the specification and claims. Such terms are to be given their ordinary meaning in the art unless otherwise indicated. Other specifically defined terms are to be construed in a manner consistent with the definitions provided herein. In order to facilitate review of the various embodiments of the disclosure, the following explanations of specific terms are provided:

As used herein, the singular forms "a," "an," and "the" include plural referents unless the content clearly dictates otherwise. Thus, for example, reference to "a cell" includes a combination of two or more cells, and the like.

The terms "about" and "approximately," when used to modify a numeric value or numeric range, indicate that deviations of 5% to 10% above and 5% to 10% below the value or range remain within the intended meaning of the recited value or range.

The term "adult" means post-embryonic. With respect to the stem cells, the term "adult stem cell" means that the stem cell is isolated from a tissue or organ of an animal at a stage of growth later than the embryonic state. In one aspect, the adult stem cells of the invention may be isolated at the post-natal stage. The adult stem cells may be isolated preferably from a mammal, such as a human. Adult stem cells according to the invention may be isolated from any non-embryonic tissue and will include neonates, juveniles, adolescents, and adult patients. Generally, the adult stem cell of the present invention will be isolated from a non-neonate mammal, more preferably from a non-neonate human. These adult stem cells are characterized in that, in their undifferentiated state, they express telomerase, do not show gap junctional intercellular communication (GJIC) and do not have a transformed phenotype.

The term "bioelectronics device" refers to an electronic device that interfaces with a living cell, tissue, or organism for clinical testing, diagnosis, and therapy. Bioelectronics devices include, but are not limited to: electronic devices for detection and characterization of biological or biochemical materials, such as on the cellular and subcellular level; devices that use biological systems in electronic applications, such as processing electronic components from DNA, nerves, or cells); and electronic devices that physically interact with biological systems (e.g., cell-electrode, protein-electrode).

The term "biomaterial" refers to material exploited in contact with living tissues, organisms, or microorganisms. Biomaterials include any substance that has been engineered to interact with biological systems for a therapeutic purpose (e.g., to treat, augment, repair, or replace a tissue function of the body) or a diagnostic purpose.

The term "cardiac arrest" is also known as heart arrest, cardiopulmonary arrest, circulatory arrest, ventricular fibrillation, sudden cardiac arrest, sudden death, sudden cardiac death, sudden arrest, asystole, clinical death, or cardioplegic arrest.

The term "cardiac dysfunction" is known to the person skilled in the art. It relates to any kind of heart dysfunction, more particularly to heart dysfunctions affecting the pumping capability, and more particularly it relates to acute and chronic cardiac events. Examples of cardiac dysfunction include, but are not limited to, heart failure, bradycardia, tachycardia, and atrial fibrillation.

The term "cardiac tissue" refers to any tissue that is present within the heart of a subject. Such cardiac tissue includes myocardium. The cardiac tissue may be from any organism possessing cardiac tissue. Preferably, the cardiac tissue is mammalian; more preferably the cardiac tissue is human. Cardiac tissue can be isolated, for example, from the hearts of sacrificed animals, from small cardiac biopsies obtained during cardiac surgery, by means of a biopsy catheter during cardiac surgery, or from donor hearts.

The term "cardioplegic arrest" refers to cardiac arrest induced by cardioplegic solution during heart surgery when heart beat needs to be stopped. Current cardioplegic solutions contain higher amounts of potassium and/or magnesium ions.

The term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or as a pharmaceutical preparation.

The term "collagenase" refers to one or more proteins exhibiting collagenase activity in a standard collagenase assay. In general, collagenases are matrix metalloproteinase enzymes (MMPs). MMPs are zinc-dependent endopeptidases capable of degrading a number of extracellular matrix proteins such as collagen, but also can process a number of bioactive molecules. Non limiting examples of collagenases include microbial collagenases, mammalian collagenases, and combinations thereof.

The term "complementary" when used in reference to a polynucleotide is intended to mean a polynucleotide that includes a nucleotide sequence capable of selectively annealing to an identifying region of a target polynucleotide under certain conditions. The term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions can also contribute to duplex stability. Conditions under which a polynucleotide anneals to complementary or substantially complementary regions of target nucleic acids are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968). Annealing conditions will depend upon the particular application, and can be routinely determined by persons skilled in the art, without undue experimentation.

The terms "comprising," "including," "having," and the like, as used with respect to embodiments, are synonymous.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

The terms "CRISPR-Cas technology" or "CRISPR-Cas system" refer to an enzyme system including a guide RNA sequence that contains a nucleotide sequence complementary or substantially complementary to a region of a target polynucleotide, and a protein with nuclease activity. CRISPR-Cas systems include Type I CRISPR-Cas system, Type II CRISPR-Cas system, Type III CRISPR-Cas system, and derivatives thereof. CRISPR-Cas systems include engineered and/or programmed nuclease systems derived from naturally accruing CRISPR-Cas systems. CRISPR-Cas systems may contain engineered and/or mutated Cas proteins. CRISPR-Cas systems may contain engineered and/or programmed guide RNA. The term "guide RNA" refers to a RNA containing a sequence that is complementary or substantially complementary to a region of a target DNA sequence. A guide RNA may contain nucleotide sequences other than the region complementary or substantially complementary to a region of a target DNA sequence. A guide RNA may be a crRNA or a derivative thereof, e.g., a crRNA: tracrRNA chimera.

Non-limiting examples of suitable Cas proteins which may be used in accordance with the present teachings include Cas3, Cas4, Cas5, Cas5e (or CasD), Cash, Cas6e, Cas6f, Cas7, Cas8a1, Cas8a2, Cas8b, Cas8c, Cas9, Cas1O, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csz1, Csx15, Csf1, Csf2, Csf3, Csf4, and Cul966. According to a specific embodiment, the Cas nuclease is Cas9. Various methods for designing CRISPR/Cas are known in the art and may be implemented in accordance with the present teachings. Further details relating to CRISPR/Cas can be found in PCT publication nos. WO 2014089290 and WO 2016125143, which are incorporated herein by reference in their entirety.

The term "culture" refers to the growth or maintenance of cells, organisms, multicellular entities, or tissue in a medium. The term "culturing" refers to any method of achieving such growth or maintenance, and may comprise multiple steps. The term "culturing" includes the cultivation of cells or tissue explants in a continuous flow of fresh medium to maintain cell growth, e.g. viability. A "cell culture" refers to a growth of cells in vitro. In such a culture, the cells proliferate, but they may not organize into a tissue per se. A "tissue culture" refers to the maintenance or growth of tissue, e.g., explants of organ primordial or of an adult organ in vitro so as to preserve its architecture and function. A "monolayer culture" refers to a culture in which cells multiply in a suitable medium while being principally attached to each other and to a substrate. Furthermore, a "suspension culture" refers to a culture in which cells multiply while suspended in a suitable medium. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture. A "confluent culture" is a cell culture in which all the cells are in contact and thus the entire surface of the culture vessel is covered, and implies that the cells have also reached their maximum density, though confluence does not necessarily mean that division will cease or that the population will not increase in size thereafter.

The term "culture medium" or "medium" is recognized in the art, and refers generally to any substance or preparation used for the cultivation of living cells or tissue. The term "medium," as used in reference to a cell or tissue culture, includes the components of the environment surrounding the cells or tissue. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells or tissue growing on a solid or semisolid support are exposed. The term "medium" also refers to material that is intended for use in a cell or tissue culture, even if it has not yet been contacted with cells or tissue. "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. The term "basal medium" refers to a medium that serves as the basis for a more complex medium, to which supplements such as serum, buffers, growth factors, lipids, and the like are added. Most basal media generally comprise of four basic chemical groups: amino acids, carbohydrates, inorganic salts, and vitamins. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IMDM). The term "fresh medium" refers to the culture medium which is rich in nutrients (such as glucose and essential amino acids) and $O_2$ but poor in metabolic waste products (such as lactate, glutamate, ammonia) and $CO_2$.

The terms "engineered" or "recombinant manipulation" refer to any sort of manipulation of the genetic material contained within a cell. This includes, by way of example only, gene insertion, gene deletion, and insertion of a promoter or other regulatory element into a cell, including insertion of an exogenous promoter or regulatory element, or insertion of an endogenous promoter or regulatory element at a position at which it would not be expected to occur.

The term "embryonic stem cell" refers to a totipotent cell isolated from a very early embryo. These cells are not differentiated and have the capacity to differentiate into ectoderm and endoderm, and further to differentiate into any of the cells in the body. The embryonic stem cell is generally isolated from a very early mammalian embryo, such as a human embryo.

The term "ex vivo" refers to a condition applied to a cell, a tissue, or other sample obtained from an organism that takes place outside of the organism. For example, an ex vivo treatment of a tissue slice obtained from an organ of a subject can include exposing the isolated tissue slice to a compound in an artificial environment (e.g., a tissue culture chamber) outside the subject.

The term "genome-wide associated study (GWAS)" refers to an examination of genetic variation across a cohort of individuals to identify genetic markers or variants that associate (correlate) with phenotypical traits.

The terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double stranded (duplex). Duplex nucleic acids may be homoduplex or heteroduplex.

The term "microbiome" refers to the totality of microbes (bacteria, fungae, protists), their genetic elements (genomes) in a defined environment. The microbiome may be of any origin—for example a gut microbiome, an oral microbiome, an intestinal microbiome, a bronchial microbiome, a skin microbiome or a vaginal microbiome. In order to analyze the microbiome, samples are taken from a subject. The subject is typically a mammalian subject—e.g. human subject. Thus, for example stool samples may be taken to analyze the gut microbiome, bronchial samples may be taken to analyze the bronchial microbiome, a saliva sample may be taken to analyze the oral microbiome, etc.

The term "microfluidic" refers to a precisely controlled small fluidic pathway that typically includes at least one dimension of about one millimeter or less. The term "fluid" refers to air, liquid, or a combination thereof. The term "fluidic" refers to system or apparatus adapted for transport of a fluid therethrough.

The terms "optional" and "optionally" mean that the subsequently described event or circumstance may or may not occur, and that the description includes instances where said event or circumstance occurs and instances where it does not.

The term "organ" refers to any group of cells or tissues that perform a specific function or group of functions (e.g., heart, lungs, brain, eye, stomach, spleen, bones, pancreas, kidneys, liver, intestines, skin, urinary bladder and sex organs).

The term "phenotype" means any property of a cell, tissue, or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), profile of secreted or cell surface proteins, bacterial or viral infection, post-translational modifications, cell proliferation, signal transduction, metabolic defects or enhancements, transcriptional activity, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell, tissue, or organism can be determined by observing a change in one or more given phenotypes (e.g., in one or more given structural or functional features such as one or more of the phenotypes indicated above) of the mutated cell, tissue, or organism compared to the same structural or functional feature(s) in a corresponding wild-type or (non-mutated) cell, tissue, or organism (e.g., a cell, tissue, or organism that in which the gene(s) have not been mutated).

The term "physiological function" is intended to mean an activity of a cell or tissue as a whole. An activity included in the term can be the magnitude or rate of a change from an initial state of a cell or tissue to a final state of the cell or tissue. An activity can be measured qualitatively or quantitatively. An activity included in the term can be, for example, growth, energy production, redox equivalent production, biomass production, compound production, development, flux through a particular reaction or set of reactions, enzyme activity, changes in gene expression, or consumption of carbon, nitrogen, sulfur, phosphate, hydrogen or oxygen. An activity can also be an output of a particular reaction that is determined or predicted in the context of substantially all of the reactions that affect the particular reaction in a cell or substantially all of the reactions that occur in a cell. Examples of a particular reaction included in the term are production of biomass precursors, production of a protein, production of an amino acid, production of a purine, production of a pyrimidine, production of a lipid, production of a fatty acid, production of a cofactor, production of a bioactive small molecule, gene transcription, flux through a particular reaction or set of reactions, enzyme activity, or transport of a metabolite. The activities or reactions in the physiological function can be increased or decreased. A physiological function can include an emergent property which emerges from the whole but not from the sum of parts where the parts are observed in isolation.

The term "physiological parameter" refers to one or more variables that measure a physiological function. Physiological parameters include, but are not limited to, functional, metabolic, or transcriptional parameters.

The term "polynucleotide" refers to a polymer of ribonucleic acid (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid. The term includes various modifications and analogues known in the art.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

The term "predetermined value" refers to a laboratory value used as a reference for values/data obtained by laboratory examinations of patients or samples collected from patients. The predetermined value can be an absolute value; a relative value; a value that has an upper and/or lower limit; a range of values; an average value; a median value, a mean value, or a value as compared to a particular control or baseline value. A predetermined value can be based on an individual sample value, such as, for example, a value obtained from a sample from the subject being tested, but at an earlier point in time. The predetermined value can be based on a large number of samples, such as from a population of subjects of the chronological age matched group, or based on a pool of samples including or excluding the sample to be tested.

The term "recombinant" with reference to a nucleic acid or polypeptide refers to one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide may also refer to a polypeptide that has been made using recombinant nucleic acids, including recombinant nucleic acids transferred to a host organism that is not the natural source of the polypeptide.

The term "solution" includes a pharmaceutically acceptable carrier or diluent in which the cells of the invention remain viable.

The term "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms "subject," "patient" and "individual" are used interchangeably herein.

The term "support" refers to any device or material that may serve as a foundation or matrix for the growth or maintenance of organ tissue (e.g., cardiac tissue slices).

The term "TALENs" or "Transcription Activator-Like Effector Nucleases" refers to the artificial restriction enzymes generated by fusing the TAL effector DNA binding domain to a DNA cleavage domain. TALENs of the invention enable efficient, programmable, and specific DNA cleavage. It will be appreciated that Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN. Further details relating to TALENS can be found in U.S. Pat. Nos. 8,450,471, 8,440,431, and 8,440,432; U.S. Patent Application No. 20140256798; and PCT publication no. WO 2016178207 A1, all of which are incorporated herein by reference in their entirety.

The term "targeted genome editing" refers to the use of engineered nucleases to introduce targeted genomic sequence changes (i.e., targeted deletions, insertions, and precise sequence changes) into living cells, tissues, and organisms. Engineered nucleases include meganucleases, zinc finger nucleases (ZFNs), and Transcription Activator-Like Effector Nucleases (TALENs). Targeted genome editing can also be accomplished using a CRISPR-Cas system. Further details relating to targeted genome editing techniques can be found in Sander, J. D. and Joung, J. K., Nat. Biotechnol. 32(4):347-55 (2014), which is incorporated herein by reference in its entirety.

The term "therapeutic agent" or "therapeutic" refers to an agent capable of having a desired biological effect on a host in vivo or a cell culture or tissue in vitro. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

The term "therapeutic virus" refers to a virus that is administered for the treatment of a disease or disorder. A therapeutic virus is typically a modified virus. Such modifications include one or more insertions, deletions, or mutations in the genome of the virus. Therapeutic viruses typically possess modifications in one or more endogenous viral genes or one or more intergenic regions, which attenuate the toxicity of the virus, and can optionally express a heterologous therapeutic gene product and/or detectable protein. Therapeutic viruses can contain heterologous nucleic acid molecules, including one or more gene expression cassettes for the expression of the therapeutic gene product and/or detectable protein. Therapeutic viruses can be replication competent viruses (e.g., oncolytic viruses) including conditional replicating viruses, or replication-defective viruses. As used herein, the term, "therapeutic gene product" refers to any heterologous protein expressed by the therapeutic virus that ameliorates the symptoms of a disease or disorder or ameliorates the disease or disorder.

The term "tissue slice" refers to a thin section, strip or sliver derived from organ tissue. Preferably, the tissue slice has a thickness less than about 1 mm, and more preferably has a thickness in the range of about 200 μm to about 500 μm. It is understood, however, that the tissue slice can have any length or width appropriate for culture.

The term "transformation" refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

The term "tropism" refers to the cells and tissues of a host that support growth of a particular virus or bacterium. Some bacteria and viruses have a broad tissue tropism and can infect many types of cells and tissues. Other viruses may infect primarily a single tissue. A "tropism modification" refers to a genetic or structural modification to a virus or bacterium resulting in altered tropism.

The term "vector" is used interchangeably with the terms "construct", "cloning vector" and "expression vector" and means the vehicle by which a DNA or RNA sequence (e.g. a foreign or heterologous gene) can be introduced into a host cell, (e.g. embryonic stem cell or pronucleus) so as to transform the host and promote expression (e.g. transcription and translation) of the introduced sequence including but not limited to plasmid, phage, transposons, retrotransposons, viral vector, and retroviral vector. By "non-viral vector" is meant any vector that does not comprise a virus or retrovirus.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Embodiments of the present disclosure are described in detail with reference to embodiments thereof as illustrated in the accompanying drawings. References to "one embodiment," "an embodiment," "some embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. The following examples are illustrative, but not limiting, of the present embodiments. Other suitable modifications and adaptations of the variety of conditions and parameters normally encountered in the field, and which would be apparent to those skilled in the art, are within the spirit and scope of the disclosure. In the drawings, like reference numbers generally indicate identical, functionally similar, and/or structurally similar elements.

II. Illustrative Embodiments of the Invention

Figure 3:
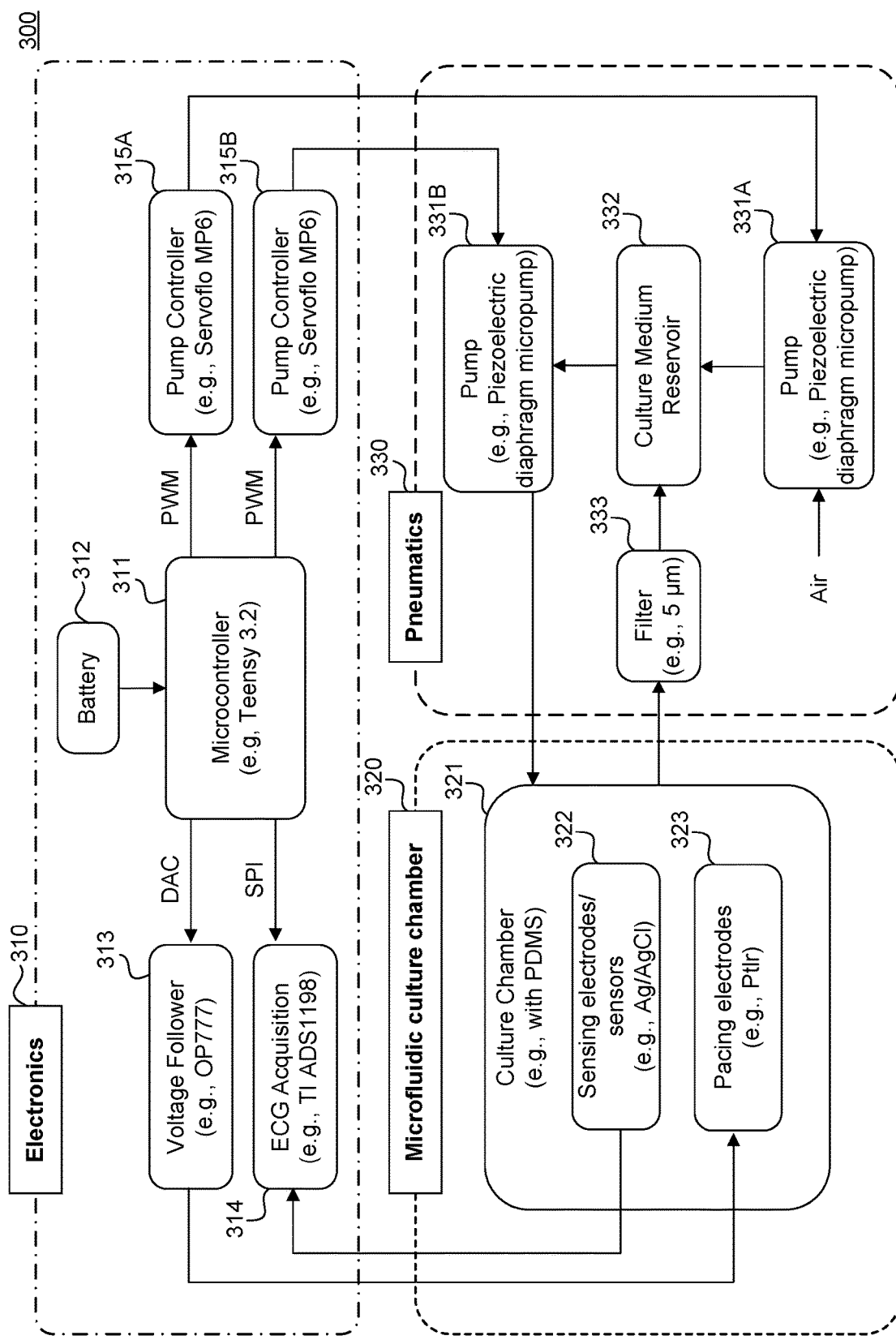
FIG. 3 depicts a block diagram of a microfluidic system for organotypic culture of cardiac slices. This dynamic culture system can be used to maintain tissue slice viability and to prevent tissue dedifferentiation.

FIG. 3 illustrates a block diagram of an example culture system 300, according to an embodiment. In some embodiments, culture system 300 can include an electronics module 310, a microfluidic culture device (or chamber) 320, and/or a pneumatics module 330. The electronics module 310 can be configured, for example, to power and/or control the components of microfluidic culture device 320 and/or the pneumatics module 330.

In some embodiments, the electronics module 310 can include a microcontroller 311, which can be used to control other components within the electronics module 310 and/or components in the microfluidic culture device 320 and/or the pneumatics module 330. The microcontroller 311 can include software, programs, logic, algorithms, etc. to operate other components of the culture system 300. In some embodiments, the electronics module 310 can include a power source, for example, a battery 312. Preferably, the battery 312 is a portable battery. The battery 312 can be coupled to the microcontroller 311.

In some embodiments, the microcontroller 311 can be coupled to actuators and sensors in microfluidic culture device 320. As shown by way of example in FIG. 3, in some embodiments, a voltage follower 313 can be coupled to one or more pacing electrodes 323 (i.e., actuators or stimulators) and an ECG acquisition module 314 can be coupled to one or more sensing electrodes (i.e., sensors) that are disposed within a culture chamber 321. Actuators/stimulators can include, but are not limited to, electrical stimulators, mechanical stimulators, chemical stimulators, optical stimulator, and other appropriate tissue stimulators. Sensors can include, but are not limited to, temperature sensors, oxygen sensors, pH sensors, humidity sensors, photodiodes, ECG sensors, and other appropriate tissue sensors.

In some embodiments, the microcontroller 311 can be coupled to one or more pump controllers configured to control one or more pumps in the pneumatics module 330. For example, as shown in FIG. 3, in some embodiments, a first pump controller 315A can be coupled to a first pump 331A and a second pump controller 315B can be coupled to a second pump 331B. In some embodiments, one or both pumps 331A, 331B can be piezoelectric pumps, for example piezoelectric diaphragm micropumps. In some embodiments, pneumatics module 330 can also include one or more of culture medium reservoir 332. For example, there can be one, two, three, four, or more culture medium reservoirs containing the same or different mediums, for example, chemicals to stimulate the tissue in microfluidic culture device 320. In some embodiments, one or both pumps 331A, 331B can pump one or more mediums into culture chamber 321 via an inlet to culture chamber 321. In some embodiments, the medium can return to the culture medium reservoir 332 via an outlet from the culture chamber 321 after passing through a filter 333.

Figure 4A:
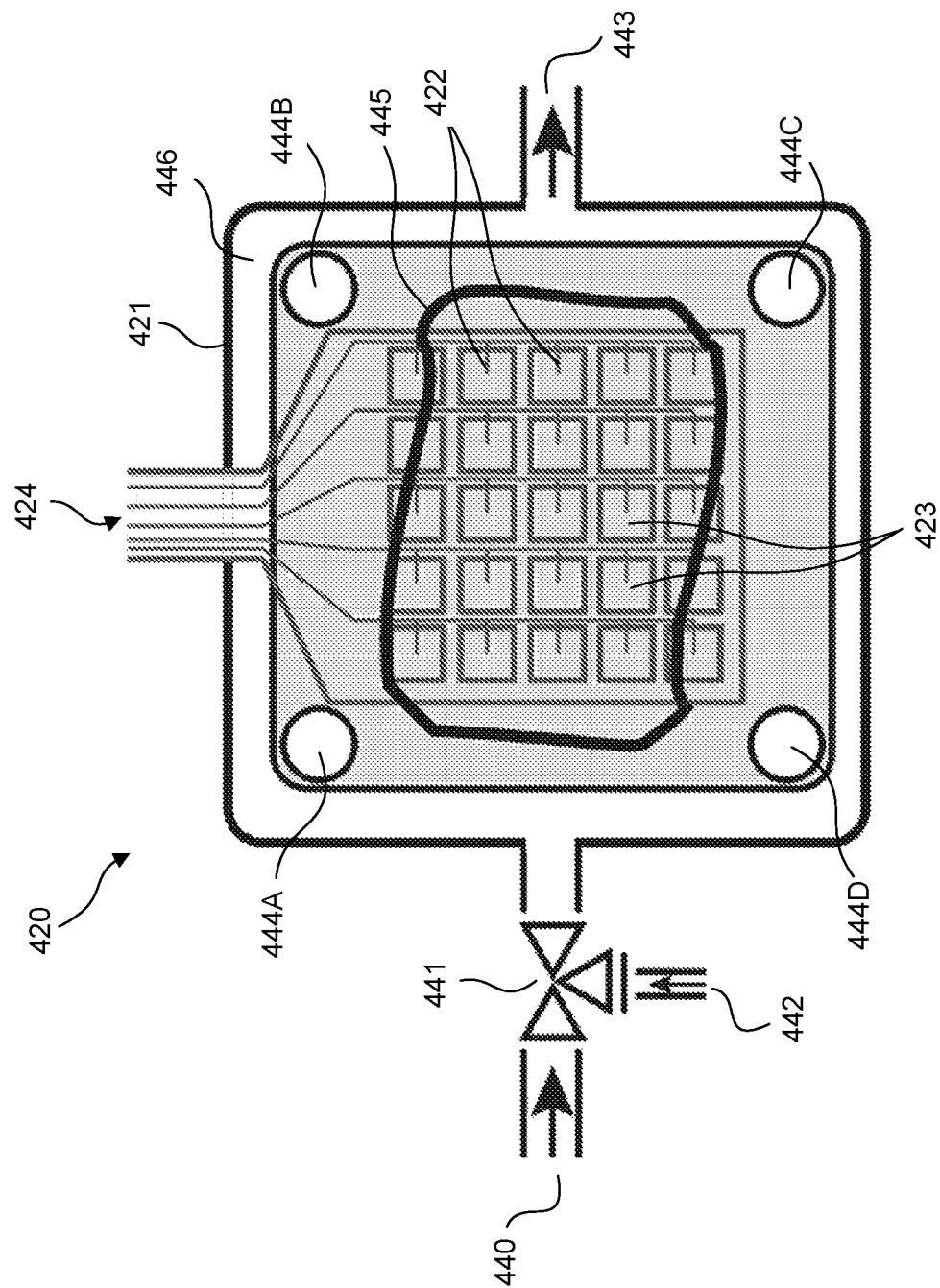
FIG. 4 depicts a top view (FIG. 4A) and a side view (FIG. 4B) of a tissue culture chamber which provides a restricted environment supplied with oxygen and nutrients necessary to maintain a desired phenotype for a tissue slice long-term.
Figure 4B:
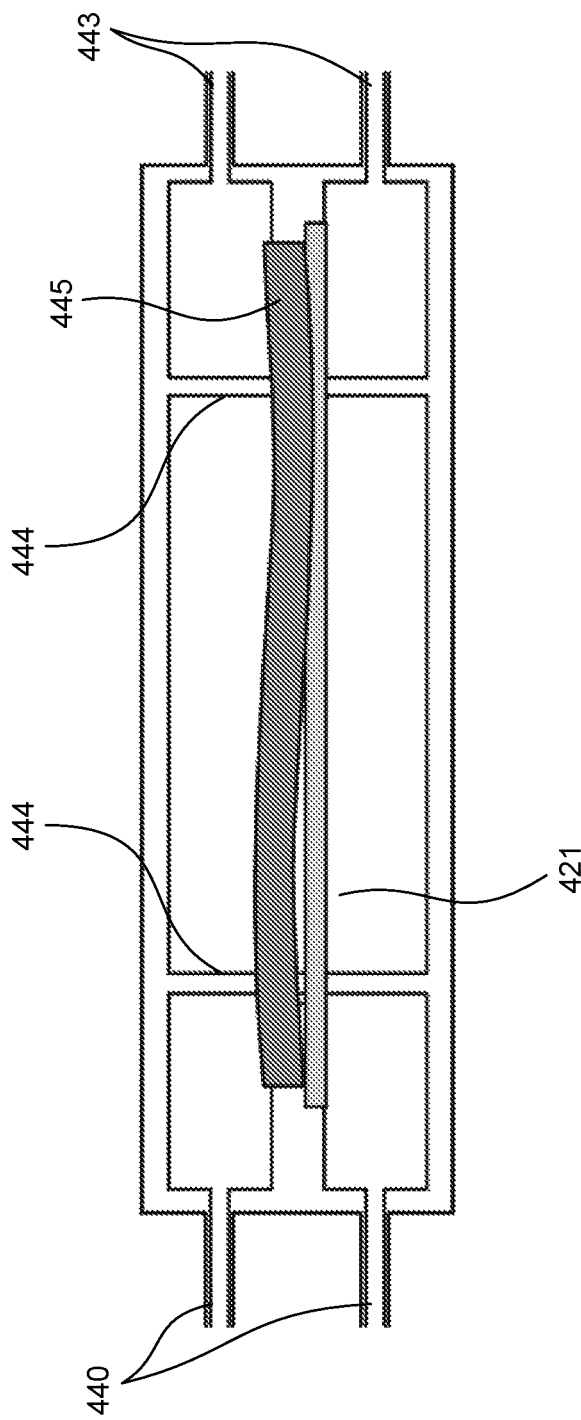

FIG. 4A illustrates an example schematic of a microfluidic culture device 420, according to an embodiment. FIG. 4B illustrates a cross-sectional view of microfluidic culture device 420, according to an embodiment. As shown by way of example in FIGS. 4A and 4B, in some embodiments, microfluidic culture device 420 can include a culture chamber 421. In some embodiments, culture chamber 421 can include a biocompatible substrate 446 (e.g., PDMS) configured to receive a tissue slice 445 (e.g., a cardiac tissue slice). In some embodiments, tissue slice 445 can be held in place by one or more mechanical loading poles 444A-444D. In some embodiments, a sensor/actuator array 424 from an electronics module can be coupled to microfluidic culture device 420. For example, one or more sensing electrodes 422 and one or more pacing electrodes 423 can be disposed in an interior of culture chamber 421 and coupled to tissue slice 445 to stimulate tissue slice 445 and obtain data from tissue slice 445. In some embodiments, culture chamber 421 can include one or more of media inlet 440, one or more of intervention inlet 442, and one or more of outlet 443.

Figure 5A:
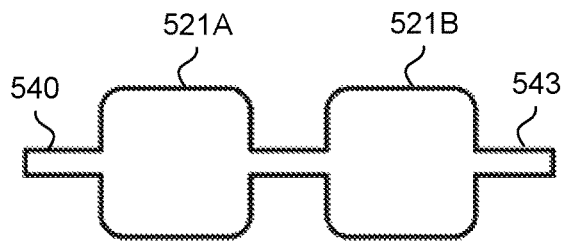
FIG. 5 depicts the configuration of two or more tissue culture chambers (e.g., microfluidic chambers) in series (FIG. 5A), parallel (FIG. 5B), or combinations thereof (FIGS. 5C-D).
Figure 5B:
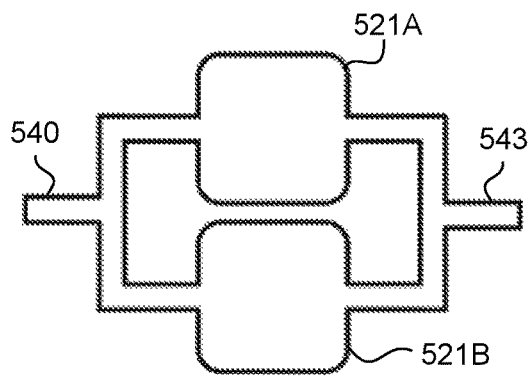
Figure 5C:
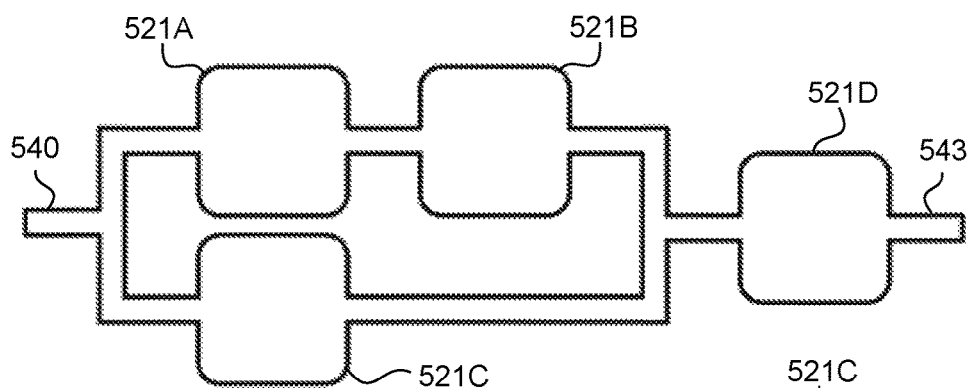
Figure 5D:
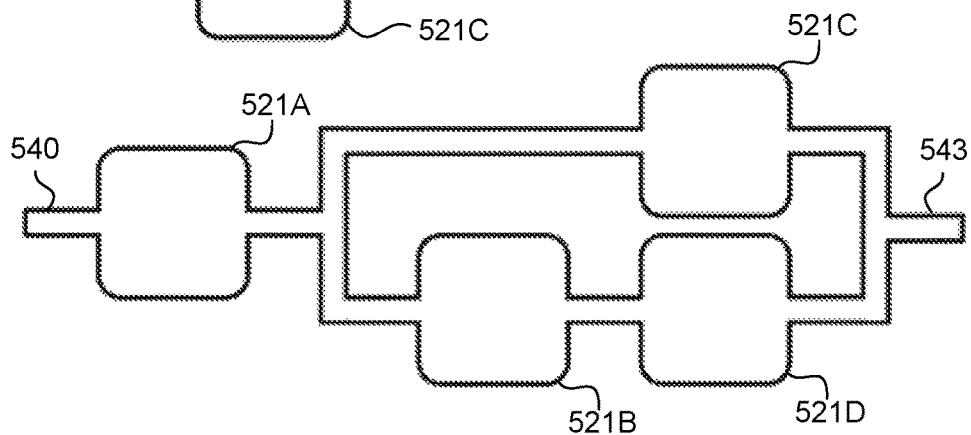

In some embodiments, the culture systems described herein can include one or more culture chambers. For example, culture systems can include one, two, three, four, five, six, or more culture chambers. FIGS. 5A-5B illustrate example arrangements of culture chambers. In each embodiment, the culture chambers have an inlet 540 and an outlet 543. FIG. 5A illustrates an embodiment where culture chamber 521A and culture chamber 521B are arranged in series. FIG. 5B illustrates an embodiment where culture chamber 521A and culture chamber 521B are arranged in parallel. FIG. 5C illustrates an embodiment where culture chamber 521A and culture chamber 521B are arranged in series, both of which are in parallel with culture chamber 521C, followed by culture chamber 521D in series. FIG. 5D illustrates an embodiment where culture chamber 521A is followed by culture chamber 521B in series with culture chamber 521D, both of which are in parallel with culture chamber 521C. Other examples and numbers of culture chambers are contemplated. For example, in some embodiments, three culture chambers can be arranged in series or all three culture chambers can be in parallel with each other.

Figure 6:
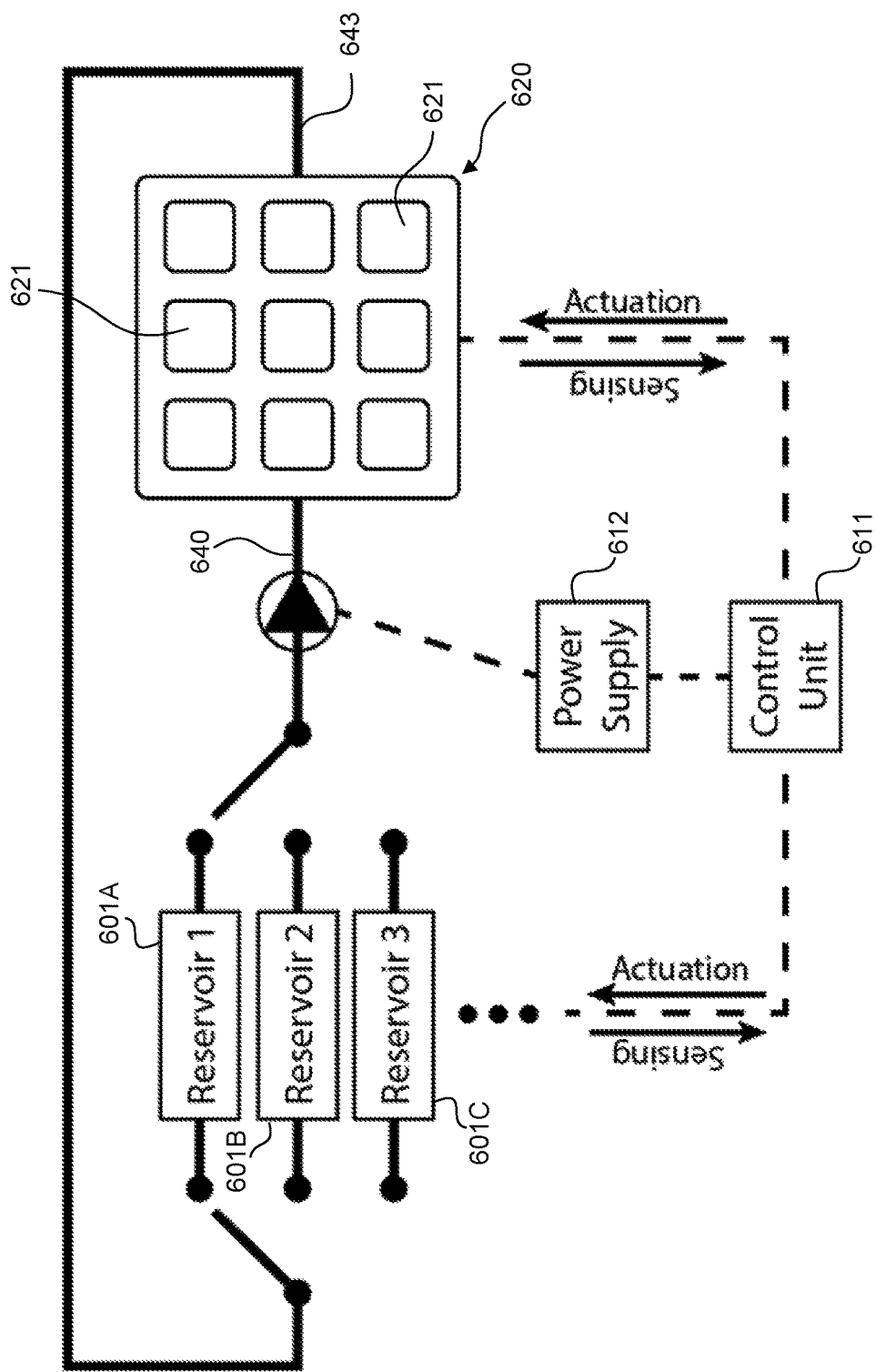
FIGS. 6 and 7 are block diagrams depicting the interface between a culture system and a control unit (e.g., a microcontroller). One or more tissue culture chambers of the culture system are instrumented with an array of actuators and sensors which allows the control unit to monitor and control components of the culture system via a wireless or wired communication. For example, the control unit can actuate the delivery of a pharmacological compound or therapeutic virus contained within the media of a media reservoir to a tissue culture chamber when specific physiological parameters are met within the tissue culture chamber.

FIG. 6 illustrates an example schematic of a culture system 600, according to an embodiment. In some embodiments, one or more reservoirs can be coupled to a microfluidic culture device. For example, as shown in FIG. 6, in some embodiments, three reservoirs 601A-601C can be coupled to microfluidic culture device 620, which can have one or more culture chambers 621 (e.g., nine culture chambers), via media inlet 640. In some embodiments, a media outlet 643 can recirculate the media to reservoirs 601A-601C. As also shown in FIG. 6, a control unit 611 (e.g., a microcontroller) and a power supply 612 (e.g., a battery) can be coupled to microfluidic culture device 620.

Figure 10:
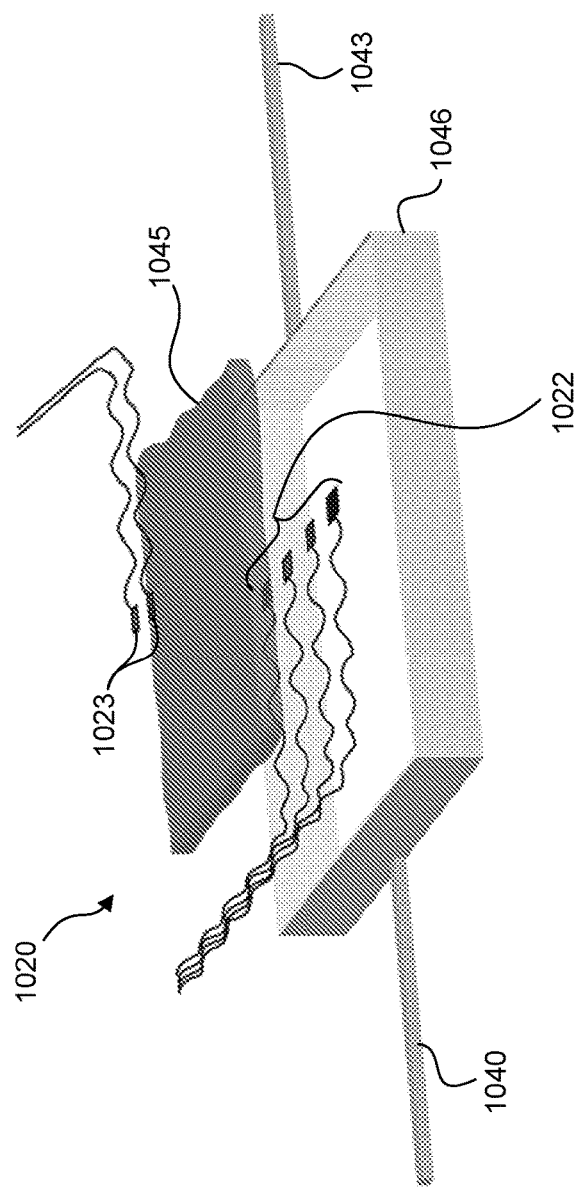
FIG. 10 depicts a microfluidic culture chamber designed for in vitro cell type reprogramming and functional characterization of cardiac slices.

FIG. 10 illustrates an example culture system 1000, according to an embodiment. As shown by way of example in FIG. 10, in some embodiments, microfluidic culture device 1020 can include a well that is made of a biocompatible substrate 1046 (e.g., PDMS) with a media inlet 1040 and a media outlet 1043. In some embodiments, a plurality of sensors 1022 (e.g., a temperature sensor, a pH sensor, a photodiode and/or an ECG sensor) and a plurality of actuators 1023 (e.g., an LED or other light source and/or an electrical, chemical, or mechanical stimulation electrode) can be disposed within the microfluidic culture device 1020. The sensors 1022 and actuators 1023 can be coupled to a tissue slice 1045 (e.g., a cardiac tissue slice). In some embodiments, the sensors 1022 can be coupled to a bottom of the tissue slice 1045 and the actuators 1023 can be coupled to a top of the tissue slice 1045, or vice versa. In some embodiments, some of the sensors 1022 can be coupled to the bottom of the tissue slice 1045 and some of the sensors 1022 can be coupled to the top of the tissue slice 1045. Likewise, in some embodiments, some of the actuators 1023 can be coupled to the bottom of the tissue slice 1045 and some of the actuators 1023 can be coupled to the top of the tissue slice 1045.

Figure 14:
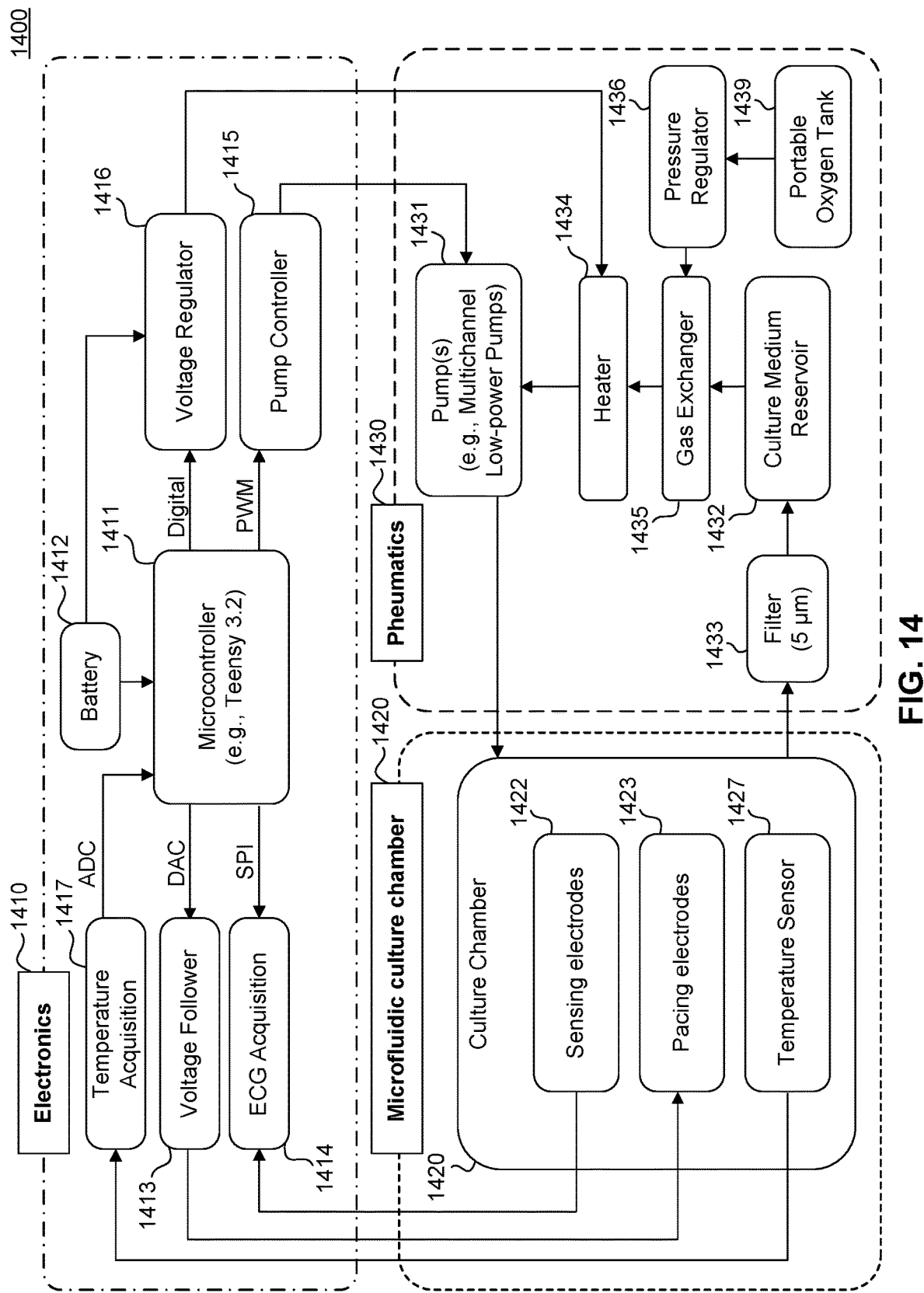
FIG. 14 depicts a block diagram of a self-contained culture system. The culture system maintains tissue slice viability by providing optimal medium circulation, oxygenation, and temperature control. To prevent tissue remodeling and dedifferentiation, the culture chambers are instrumented with pacing electrodes for electrical stimulation. The culture system is controlled by a microcontroller (e.g., Teensy 3.2). Power is supplied by a battery (e.g., a 5V 30,000 mAh battery). Medium circulation is driven by a pump (e.g., a low-power, multichannel syringe pump). Medium temperature and oxygenation is maintained by a custom gas exchanger and heater unit. Temperature sensors are built into the culture chambers for feedback control. A multichannel ECG can be measured simultaneously.

Similar to FIG. 3, FIG. 14 illustrates a block diagram of an example culture system 1400, according to an embodiment. In some embodiments, culture system can include an electronics module 1410, a microfluidic culture device (or chamber) 1420, and/or a pneumatics module 1430. The electronics module 1410 can be configured, for example, to power and/or control the microfluidic culture device 1420 and/or the pneumatics module 1430.

In some embodiments, the electronics module 1410 can include a microcontroller 1411, which can be used to control other components within the electronics module 1410 and/or components in the microfluidic culture device 1420 and/or the pneumatics module 1430. The microcontroller 1411 can include software, programs, logic, algorithms, etc. to operate other components of the culture system 1400. In some embodiments, the electronics module can include a power source, for example, a battery 1412. Preferably, the battery 1412 is a portable battery. The battery 1412 can be coupled to the microcontroller 1411.

In some embodiments, the microcontroller 1411 can be coupled to actuators and sensors in the microfluidic culture device 1420. As shown by way of example in FIG. 14, in some embodiments, a voltage follower 1413 can be coupled to one or more pacing electrodes 1423 (i.e., actuators or stimulators) and an ECG acquisition module 1414 can be coupled to one or more sensing electrodes (i.e., sensors) that are disposed within a culture chamber 1421. Actuators/stimulators can include, but are not limited to, electrical stimulators, mechanical stimulators, chemical stimulators, optical stimulator, and other appropriate tissue stimulators. Sensors can include, but are not limited to, temperature sensors, oxygen sensors, pH sensors, humidity sensors, photodiodes, ECG sensors, and other appropriate tissue sensors. For example, FIG. 14 additionally illustrates a temperature acquisition module 1417 coupled to a temperature sensor 1427.

In some embodiments, the microcontroller 1411 can be coupled to one or more pump controllers configured to control one or more pumps in the pneumatics module 1430. For example, as shown in FIG. 14, in some embodiments, a pump controller 1415 can be coupled to a pump 1431. In some embodiments, pump 1431 can be a multichannel low power pump, for example, a peristaltic pump. In some embodiments, pneumatics module 1430 can also include one or more of culture medium reservoir 1432. For example, there can be one, two, three, four, or more culture medium reservoirs containing the same or different mediums, for example, chemicals to stimulate the tissue in microfluidic culture device 1420. In some embodiments, pump 1431 can pump one or more mediums into culture chamber 1421 via an inlet to culture chamber 1421. In some embodiments, the medium can return to the culture medium reservoir 1432 via an outlet from the culture chamber 1421 after passing through a filter 1437.

In some embodiments, pneumatics module 1430 can include an oxygen tank 1439 and a pressure regulator 1436 coupled to the oxygen tank 1439. In some embodiments, pneumatics module 1430 can also include a gas exchanger 1435 and a heater 1434. In some embodiments, one or both of the pressure regulator 1436 and culture medium reservoir can be coupled to the gas exchanger 1435. In some embodiments, the medium can be heated by the heater 1434 before being pumped into culture chamber 1421 by pump 1431.

Figure 15:
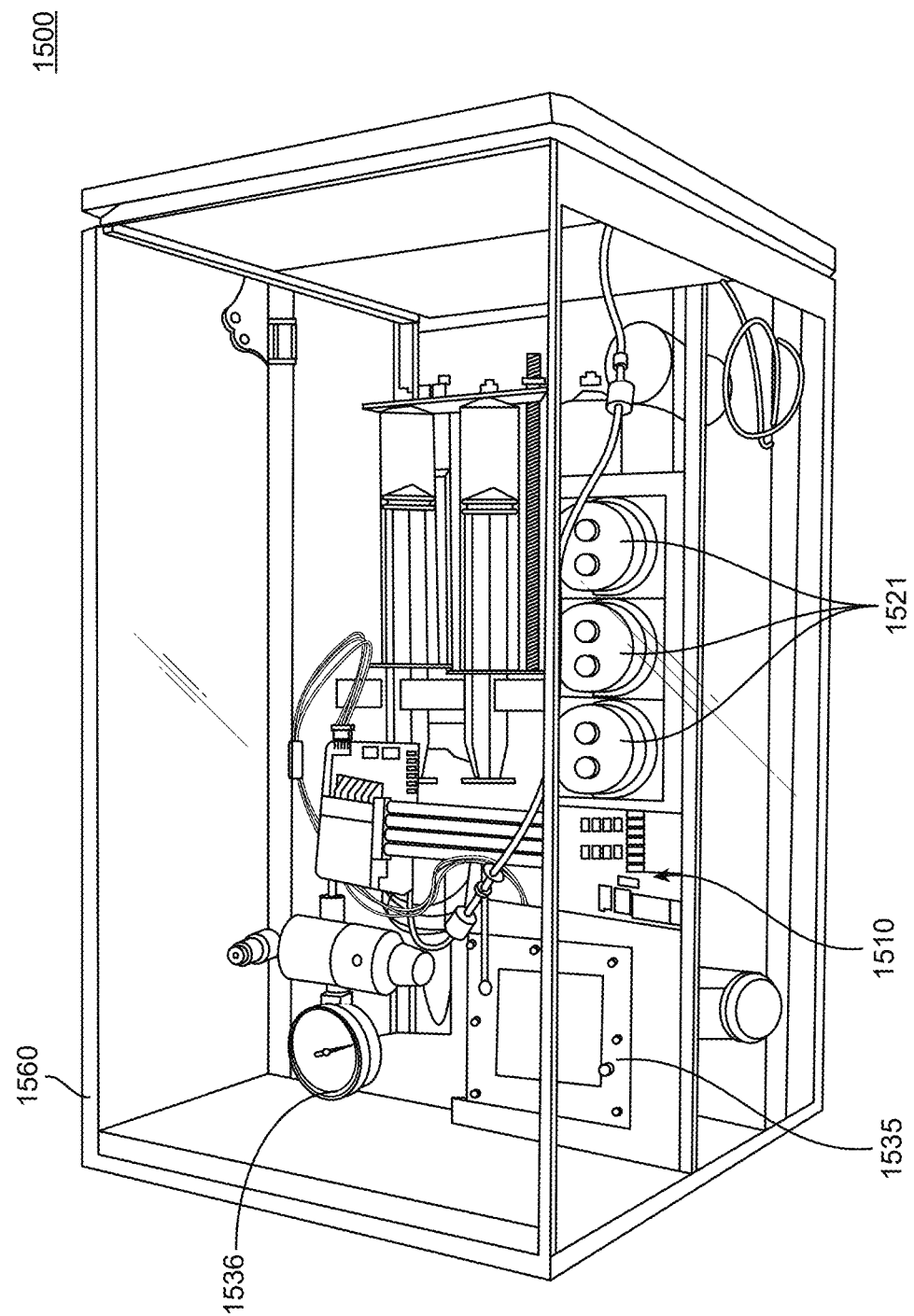
FIG. 15 illustrates an example of an assembled culture system. Insulation foam was removed from the sides of the enclosure for illustration of the assembled culture system.

FIG. 15 illustrates an example culture system 1500, according to an embodiment. As in other examples described herein, in some embodiments, culture system 1500 can include an electronics module 1510, one or more culture chambers 1521 (e.g., three culture chambers), a gas exchanger 1535, a pressure regulator 1536, or any other system component described herein. FIG. 15 also illustrates housing 1560, which can enclose the other components of the system (i.e., the other components are disposed within housing 1560). A housing can be included in any of the culture system embodiments described herein. The housing 1560 can protect and/or isolate the other system components from the surrounding environment, for example, during transport. In some embodiments, the housing can include multiple pieces such that a portion of the housing can be removed so that the other system components can be accessed.

In some embodiments, housing 1560 can have a volume of less than about 50,000 cm$^3$. In some embodiments, housing 1560 can have a volume of less than about 20,000 cm$^3$. In some embodiments, housing 1560 can have a volume of less than about 15,000 cm$^3$. In some embodiments, housing 1560 can have a volume of about 12,000 cm$^3$. In some embodiments, housing 1560 can have a volume between about 5,000 cm$^3$ and about 20,000 cm$^3$. In some embodiments, housing 1560 can have a volume between about 10,000 cm$^3$ and about 15,000 cm$^3$. The relatively small size of culture system 1500 allows for shipping of the system, for example, by car, truck, train, or plane. In some embodiments, each dimension (i.e., length, width, and height) of housing 1560 can be less than about 50 cm. In some embodiments, each dimension of housing 1560 can be less than about 40 cm. In some embodiments, each dimension of housing 1560 can be less than about 30 cm. In some embodiments, the dimensions of the housing 1560 can be about 30 cm×20 cm×20 cm.

Figure 16A:
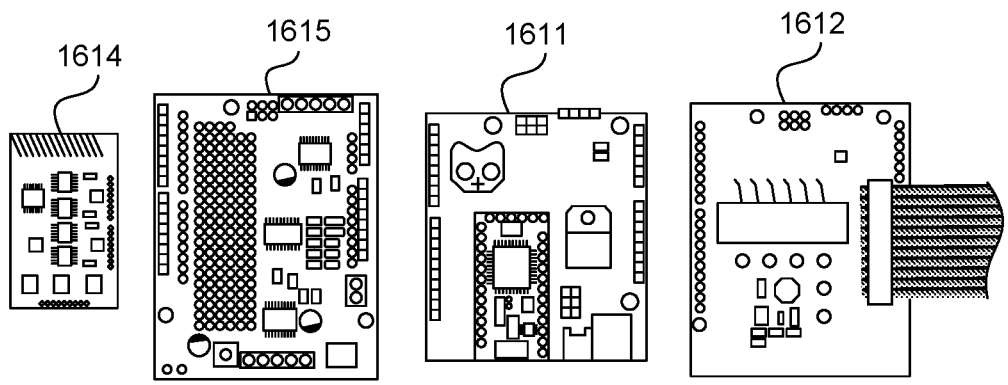
FIG. 16A shows an example of a modular electronic control unit. The electronic components of the modular electronic control unit comprise, from left to right, an acquisition module (for ECG and temperature sensing), a motor driver (e.g., a pump driver), a microcontroller, and a power management module (for supplying suitable voltages required for electrical stimulation and medium temperature control).
Figure 16B:
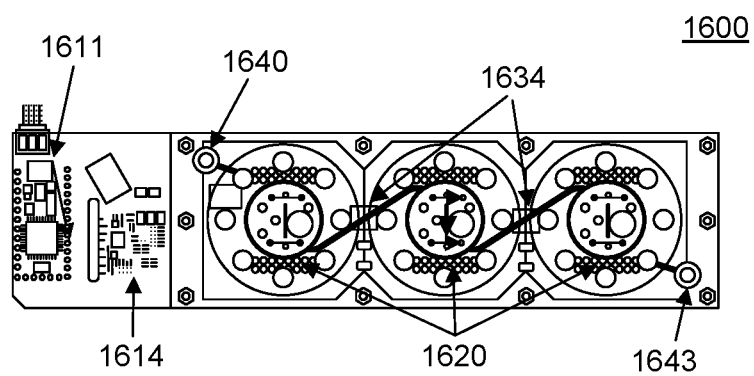
FIG. 16B illustrates a fully integrated device that is designed for compactness and comprises a microcontroller, an ECG module, a solution inlet, a solution outlet a thermoelectric heater/cooler, and three tissue culture chambers disposed in series.
Figure 16C:
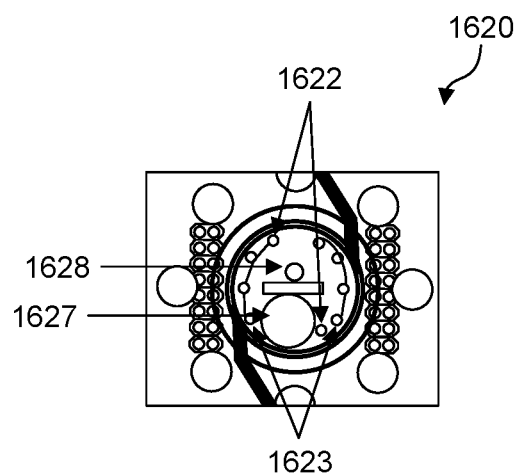
FIG. 16C illustrates a tissue culture chamber instrumented with sensing electrodes, field pacing electrodes, a temperature sensor, and an LED.

FIGS. 16A-16C illustrate example components of a culture system 1600, according to embodiments. FIG. 16A illustrates an example microcontroller 1611, power management module 1612, acquisition module 1614, and pump driver 1615 as separate components, according to an embodiment. FIG. 16B illustrates an example integrated device including a microcontroller 1611 with an acquisition module 1614 (e.g., an ECG module), a media inlet 1640, three microfluidic culture devices 1620 with heaters 1634 disposed between each microfluidic culture device 1620, and a media outlet 1643. FIG. 16C illustrates an example microfluidic culture device 1620 having sensing electrodes 1622, pacing electrodes 1623, a temperature sensor 1627, and an LED 1628.

Figure 17:
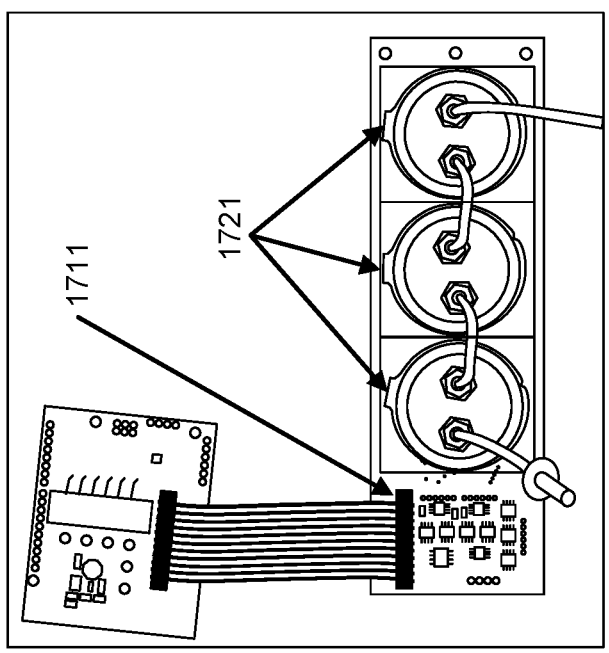
FIG. 17 illustrates an example of a culture system that is modular in design for ease of scaling up culture capacity.

FIG. 17 illustrates an example culture system, according to an embodiment, having a microcontroller 1711 coupled to a plurality of culture chambers 1721. As shown in FIG. 17, the culture chambers 1721 are disposed in series.

Figure 19:
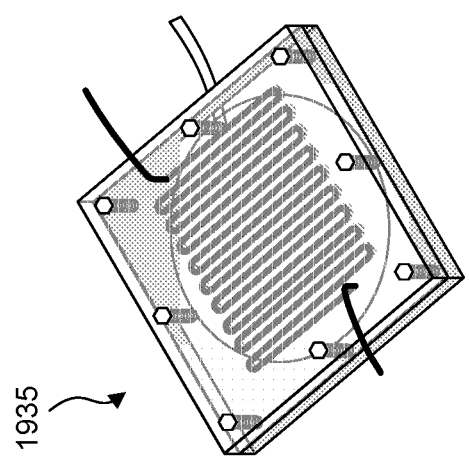

FIG. 19 illustrates an example gas exchanger 1935, according to an embodiment. To maintain viability of cultured tissue, the liquid culture medium needs to be oxygenated. Bubbling the liquid medium would result in foaming and loss of the medium. The gas exchanger comprises two chambers separated by a gas-permeable PDMS membrane. The top chamber is pressurized with gas (e.g., $O_2$ and $CO_2$). The culture medium flows through the bottom chamber. The bottom chamber also has a built-in heating element for controlling the temperature of the culture medium. The culture medium is heated and oxygenated when circulated through the gas exchanger.

Figure 20:
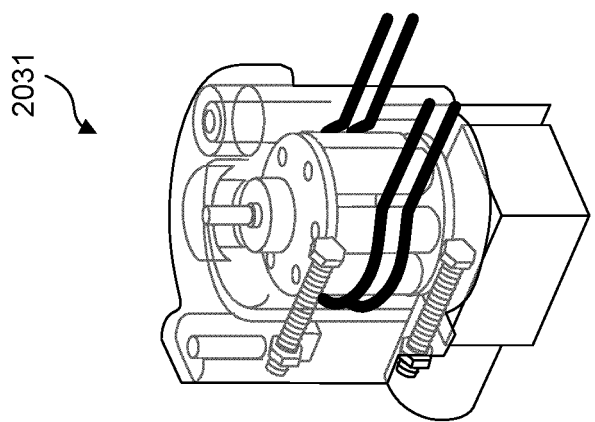

FIG. 20 illustrates an example of a custom 3D printed peristaltic pump, according to an embodiment. A number of commercially available pumps were evaluated and found to be inadequate with respect to their power consumption, flowrate, and/or reliability. The custom 3D printed peristaltic pump has a flow rate of 2 mL/min and power consumption of 1 W and can achieve continuous runtime of more than a week before servicing is required. To achieve these criteria, the pump comprises a 3D printed housing that allows for adjustable clamping force and a 6 roller pump head. All rotating components are connected with low-friction bearings.

Figure 21:
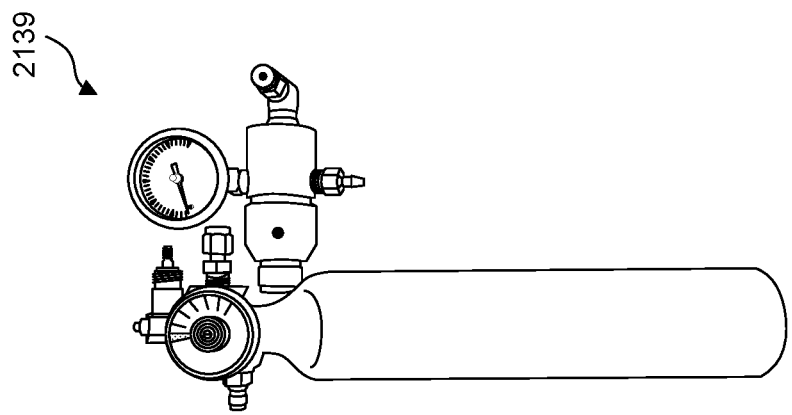
FIGS. 19-23 provide an overview of the custom gas exchanger, medium heater, and pump (for maintaining culture medium oxygenation, temperature, and circulation) of the culture system.

FIG. 21 illustrates an example portable gas tank 2139, according to an embodiment. The portable gas tank comprises a miniature pressure regulator. The portable gas tank and miniature pressure regulator were selected based on their size and performance. The gas tank can be pressurized up to 2100 psi, supporting 3 weeks of culture. The miniature pressure regulator maintains a constant pressure of 5-15 psi inside the gas exchanger.

Figure 29B:
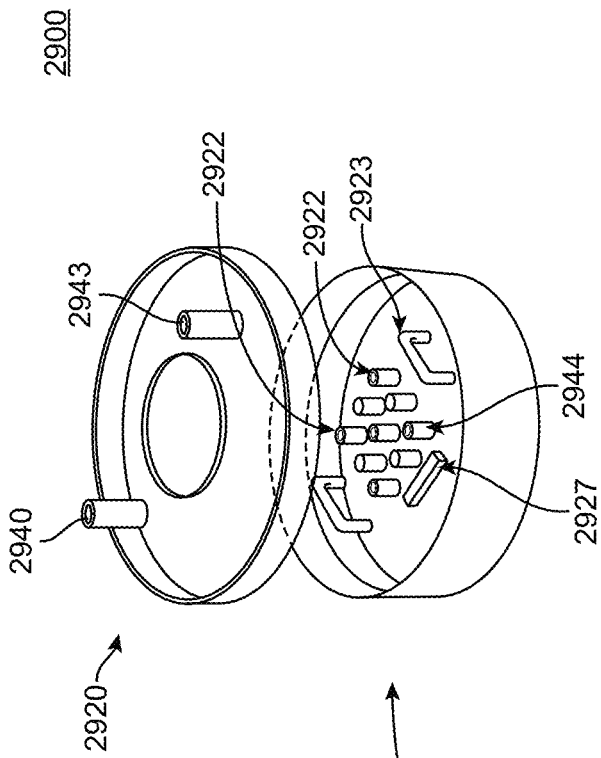
FIG. 29 depicts additional systems implemented in a heart-on-a-chip culture system for automated multiparametric characterization of cardiac slices. The culture system may comprise a miniaturized optical mapping system (FIG. 29A). The miniaturized optical mapping system can be used for measuring transmembrane action potential, calcium concentration and the metabolic state of cultured slices on a motorized stage. A multi-electrode array system is implemented in the tissue culture chambers for real-time functional monitoring of the slices (FIG. 29B).
Figure 29A:
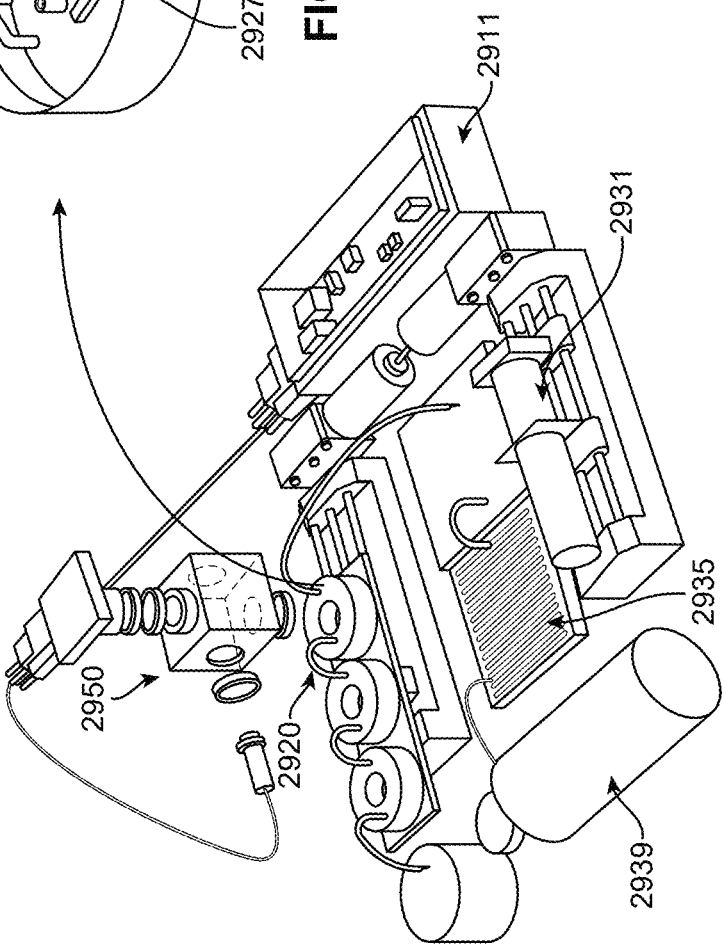

FIGS. 29A-29B illustrate culture system 2900, according to an embodiment. As shown by way of example in FIGS. 29A-29B, in some embodiments, culture system 2900 can include an electronic control/data acquisition system 2911, a microfluidic culture device 2920, a pump (e.g., a syringe pump) 2931, a gas exchanger 2935, a gas tank (e.g., an oxygen and/or carbon dioxide tank) 2939, and an optical mapping system 2950. FIG. 29B illustrates additional components of microfluidic culture device 2920, according to an embodiment. Microfluidic culture device 2920 can include a media inlet 2940, a media outlet 2943, sensing electrodes 2922, pacing electrodes 2923, a temperature sensor 2927, and mechanical loading poles 2944.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

III. Systems for Maintaining and Analyzing Tissue Slices

The present invention provides a system for maintaining and analyzing tissue slices, comprising: a microfluidic device comprising at least one tissue culture chamber; one or more actuators disposed in an interior of the tissue culture chamber; one or more sensors disposed in the interior of the tissue culture chamber; and an electronics module comprising a microcontroller, wherein the electronics module is coupled to the one or more actuators and the one or more sensors by an array of electrodes. In some embodiments, the one or more actuators comprises at least one of an electrical stimulator, a mechanical stimulator, a chemical stimulator, and an optical stimulator. In some embodiments, the one or more sensors comprises at least one of a temperature sensor, an oxygen sensor, a pH sensor, a humidity sensor, one or an array of photodetectors, a force transducer, and an electrical sensor.

In certain embodiments, the electronics module is configured to control the one or more actuators and receive data from the one or more sensors. In some embodiments, the electronics module further comprises an integrated power supply. In some embodiments, the power supply is a battery.

In certain embodiments, the system further comprises a central control unit coupled to the microcontroller, wherein the central control unit is configured to analyze data from the one or more sensors. In some embodiments, the central control unit is wirelessly coupled to the microcontroller.

In certain embodiments, a bottom portion of the at least one tissue culture chamber further comprises a substrate configured to receive a tissue slice. In some embodiments, the substrate is polydimethylsiloxane (PDMS). In certain embodiments, the PDMS matches a stiffness of the tissue slice.

In certain embodiments, the tissue slice is cardiac tissue.

In certain embodiments, the system further comprises a plurality of mechanical loading poles configured to secure the tissue slice within the tissue culture chamber. In some embodiments, the mechanical loading poles provide mechanical stimulation to the tissue slice. In some embodiments, the mechanical loading poles measure contractile force of the tissue slice.

In certain embodiments, the microfluidic device comprises two or more tissue culture chambers, each tissue culture chamber having one or more actuators disposed in an interior of the tissue culture chamber and one or more sensors disposed in the interior of the tissue culture chamber, wherein the electronics module is coupled to the one or more actuators and the one or more sensors of each tissue culture chamber. In some embodiments, the two or more tissue culture chambers are connected in series, in parallel, or any combination thereof.

In certain embodiments, the system further comprises a media reservoir, wherein the media enters the tissue culture chamber through an inlet and exits the tissue culture chamber through an outlet. In some embodiments, system further comprises at least one pump configured to deliver the media to the tissue culture chamber. In some embodiments, the pump is a piezoelectric pump, a peristaltic pump, or a syringe pump.

In certain embodiments, the system further comprises an oxygen tank, a gas exchanger, and a heater.

In certain embodiments, the system further comprises a housing, wherein the microfluidic device and the electronics module are disposed within the housing. In some embodiments, the housing is a heat and oxygen insulating housing. In some embodiments, a volume of the housing is from about 5,000 cubic centimeters to about 20,000 cubic centimeters. In some embodiments, the volume of the housing is from about 10,000 cubic centimeters to about 15,000 cubic centimeters. In some embodiments, the volume of the housing is about 30 cm by about 20 cm by about 20 cm.

IV. Methods for Maintaining Tissue Slices in a Microfluidic Device

The present invention further provides a method for maintaining one or more tissue slices in a microfluidic device, the method comprising culturing the one or more tissue slices in the microfluidic device, wherein the tissue slices are obtained from one or more organs, and wherein the microfluidic device comprises: a) one or more tissue culture chambers, wherein each tissue culture chamber provides a restricted environment supplied with oxygen and nutrients necessary to maintain a desired phenotype for each tissue slice; b) one or more actuators for maintenance of the one or more tissue slices or for phenotypic interrogation of the one or more tissue slices; c) one or more sensors for measuring one or more physiological parameters of the one or more tissue slices; and d) an electronics module comprising a microcontroller, wherein the electronics module is coupled to the one or more actuators and the one or more sensors by an array of electrodes.

In certain embodiments, the method further comprises the step of electrically, mechanically, optically, or chemically stimulating the one or more tissue slices.

In certain embodiments, the method further comprises the step of measuring the one or more physiological parameters of the one or more tissue slices.

In certain embodiments, the method further comprises the steps of electrically, mechanically, optically, or chemically stimulating the one or more tissue slices and measuring the one or more physiological parameters of the one or more tissue slices. In some embodiments, the method further comprises the step of analyzing the phenotype of the one or more tissue slices.

In certain embodiments, the phenotype of the one or more tissue slices is interrogated by (1) electrically, mechanically, optically, or chemically stimulating the one or more tissue slices, (2) measuring the one or more physiological parameters of the one or more tissue slices, and (3) analyzing the phenotype of the one or more tissue slices. In some embodiments, the desired phenotype of the tissue slice is maintained in the tissue culture chamber by electrically, mechanically, optically, or chemically stimulating the tissue slice to maintain the desired phenotype after the step of analyzing the phenotype of the one or more tissue slices.

In certain embodiments, the desired phenotype of the tissue slice is maintained in the tissue culture chamber by (1) measuring the one or more physiological parameters of the tissue slice, (2) analyzing the phenotype of the tissue slice, and (3) electrically, mechanically, optically, or chemically stimulating the tissue slice to maintain the desired phenotype.

In certain embodiments, the physiological parameters are functional, metabolic, or transcriptional parameters. In some embodiments, the physiological parameters are functional, metabolic, or transcriptional parameters. In some embodiments, the functional parameters are electrical parameters or mechanical parameters.

In certain embodiments, the one or more actuators comprise at least one of an electrical stimulator, a mechanical stimulator, a chemical stimulator, and an optical stimulator.

In certain embodiments, the one or more sensors comprise at least one of a temperature sensor, an oxygen sensor, a pH sensor, a humidity sensor, one or an array of photodetectors, a force transducer, and an electrical sensor.

In certain embodiments, the electronics module is configured to control the one or more actuators and receive date from the one or more sensors.

In certain embodiments, the microfluidic device further comprises a central control unit, wherein the central control unit is coupled to the microcontroller, and wherein the central control unit is configured to analyze date from the one or more sensors. In some embodiments, the central control unit is wirelessly coupled to the microcontroller.

In certain embodiments, a bottom portion of the one or more tissue culture chambers comprises a substrate configured to receive the tissue slice. In some embodiments, the substrate is polydimethylsiloxane (PDMS). In some embodiments, the PDMS matches a stiffness of the cultured tissue. In some embodiments, the substrate is a biocompatible porous substrate.

In certain embodiments, the one or more tissue culture chambers further comprise a plurality of mechanical loading poles, wherein the plurality of mechanical loading poles are configured to secure the tissue slice within the tissue culture chamber. In some embodiments, the mechanical loading poles provide mechanical stimulation to the tissue slice. In some embodiments, the mechanical loading poles measure contractile force of the tissue slice.

In certain embodiments, the electronics module further comprises an integrated power supply. In some embodiments, the integrated power supply is a battery.

In certain embodiments, the microfluidic device further comprises a media reservoir, wherein media enters the tissue culture chamber through an inlet and exits the tissue culture chamber through an outlet. In some embodiments, the microfluidic device further comprises at least one pump configured to deliver the media to the tissue culture chamber. In some embodiments, the pump is a piezoelectric pump, a peristaltic pump, or a syringe pump.

In certain embodiments, the microfluidic device further comprises an oxygen tank, a gas exchanger, and a heater.

In certain embodiments, the microfluidic device is a self-contained culture system designed for long-distance transportation, wherein the self-contained culture system comprises an integrated power supply, an oxygen tank, a gas exchanger, a heater, a pump, and a media reservoir, and wherein the self-contained culture system maintains viability of the one or more tissue slices during long-distance transportation by providing optimal medium circulation, oxygenation, temperature control, and stimulation.

In certain embodiments, the one or more organs are human, murine, rabbit, swine, or canine organs.

In certain embodiments, at least one tissue slice is obtained from biopsy of the one or more organs.

In certain embodiments, the one or more organs are selected from the group consisting of: brain, heart, lung, liver, kidney, spleen, and skin. In some embodiments, at least one tissue slice is obtained from a heart. In some embodiments, the at least one tissue slice obtained from a heart is an atrial or ventricular tissue slice. In some embodiments, the one or more tissue culture chambers comprise field or point pacing electrodes. In some embodiments, the one or more tissue culture chambers further comprise bipolar sensing electrodes for pseudo ECG recording or an array of unipolar electrodes for measuring electrical conduction. In some embodiments, the pacing electrodes and sensing electrodes are platinum-iridium (Pt/Ir) electrodes. In some embodiments, the pacing electrodes and sensing electrodes are fabricated into the culture chamber for electrical stimulation and sensing. In some embodiments, pacing parameters are user or software adjustable to allow for optimization of a pacing protocol during culture.

In certain embodiments, the method further comprises the step of inducing cardiac dysfunction by chronic pathological stimulation of the at least one tissue slice obtained from a heart. In some embodiments, the chronic stimulation is alpha-adrenergic, beta-adrenergic, or adenosine stimulation. In some embodiments, the cardiac dysfunction is selected from the group consisting of: heart failure, bradycardia, tachycardia, and atrial fibrillation.

In certain embodiments, the at least one tissue slice is obtained from a human donor heart rejected for transplantation or an explanted human heart. In some embodiments, the heart is cardioplegically arrested following aortic cross-clamp.

In certain embodiments, the microfluidic device is interfaced with a second microfluidic device housing a plurality of microorganisms representing a human microbiome.

In certain embodiments, the microfluidic device comprises two or more tissue slices housed in two or more tissue culture chambers connected in series, in parallel, or any combination thereof. In some embodiments, the two or more tissue slices are obtained from two or more organs. In some embodiments, the two or more organs are different types of organs. In some embodiments, the different types of organs are from the same donor. In some embodiments, the different types of organs are from different donors. In some embodiments, the two or more organs are the same type of organ obtained from different donors. In some embodiments, the two or more tissue slices are cultured in two or more tissue culture chambers configured for interrogating organ interaction. In some embodiments, the two or more tissue slices comprise a native tissue slice and an engineered tissue slice, and wherein the native tissue slice and the engineered tissue slice are cultured in tissue culture chambers configured for interrogating interaction between the native tissue slice and the engineered tissue slice. In some embodiments, the two or more tissue slices are cultured in two or more tissue culture chambers connected in series to increase throughput of pre-clinical trials. In some embodiments, the two or more tissue slices are cultured in two or more tissue culture chambers connected in parallel to test drugs at different concentrations. In some embodiments, the two or more tissue slices in two or more tissue culture chambers are exposed to different environments.

In certain embodiments, the microfluidic device comprises a real time digital or analog instrumentation that provides readouts from the one or more sensors. In some embodiments, the microfluidic device comprises a real time digital instrumentation and an analog instrumentation that provide readouts from the one or more sensors. In some embodiments, the method further comprises the step of monitoring the physiological condition of at least one tissue slice based on readouts provided by the instrumentation.

In certain embodiments, the method further comprises the step of treating at least one tissue slice with a therapeutic virus comprising a therapeutic gene product. In some embodiments, the method further comprises the step of treating the at least one tissue slice with an enzyme prior to treatment with the virus to improve transduction efficiency. In some embodiments, the enzyme is collagenase or a trypsin. In some embodiments, the virus is delivered via multiple microinjections using microcapillary needles to achieve uniform and sufficient viral transduction of the tissue slice. In some embodiments, the virus is selected from the group consisting of: adenovirus, lentivirus, and adeno-associated virus. In some embodiments, the virus has a tropism-modification and carries a cell type specific promoter for high efficiency, targeted gene delivery to different cell types in the tissue slices.

In certain embodiments, the method further comprises the step of seeding cells on at least one tissue slice for studying cell therapy. In some embodiments, the cells are mammalian or bacterial cells. In some embodiments, the mammalian or bacterial cells are engineered cells. In some embodiments, the mammalian cells are genetically transformed cells. In some embodiments, the mammalian cells are cells derived from adult stem cells or embryonic stem cells.

In certain embodiments, the method further comprises the step of performing a gene-editing technique on at least one tissue slice for targeted genome editing. In some embodiments, the gene-editing technique is based on CRISPR/Cas or TALENS technology. In some embodiments, the gene-editing technique is based on CRISPR/Cas9 technology. In some embodiments, the gene-editing technique is used to create one or more mutations at a locus identified by a genome-wide associated study (GWAS). In some embodiments, the gene-editing technique is used to correct one or more mutations at a locus.

In certain embodiments, the method further comprises the step of evaluating the performance of an implantable bioelectronics device built into the tissue culture chamber. In some embodiments, the implantable bioelectronics device is a soft, conformal device. In some embodiments, the implantable bioelectronics device is biodegradable.

In certain embodiments, the method further comprises the steps of culturing the one or more tissue slices with biomaterial and evaluating the safety or efficacy of the biomaterial.

In certain embodiments, the method further comprises the step of exposing the one or more tissue slices to one or more physical fields. In some embodiments, the one or more physical fields are selected from the group consisting of: electrical radiation, magnetic radiation, alpha-radiation, beta-radiation, and gamma-radiation.

In certain embodiments, a plurality of treatment and modalities are used to study synergistic cardiotoxicity of multiple pre-clinical drugs combined.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The following examples are provided to describe the embodiments described herein with greater detail. They are intended to illustrate, not to limit, the embodiments.

EXAMPLES

Example 1

Methods and Devices for Organotypic Human Cardiac Slice Culture a. Preparative Methods of Organotypic Human Slice Culture Adult human hearts were procured as failing human hearts and as donor human hearts. Informed donor consents were obtained for all tissue. Methods described in this section were performed in accordance with all human research guidelines. Explanted hearts were cardioplegically arrested with a high potassium solution (110 mmol/L NaCl; 1.2 mmol/L $CaCl_2$; 16 mmol/L KCl; 16 mmol/L $MgCl_2$; 10 mmol/L $NaHCO_3$) and were cooled to +4° C. in the operating room following aortic cross-clamp. Failing hearts were perfused through both coronaries, while donor hearts were perfused systemically prior to removal from the chest. The heart was maintained at this low temperature to preserve tissue during the transportation time from the operating room to the research laboratory, ranging between 15 minutes and 6 hours.

Upon arrival, an approximately one-inch cube of ventricular or atrial tissue was cut in cardioplegic solution. For example, left ventricular tissue was taken from a region close to the left anterior descending artery and circumflex artery. Atrial tissue was taken from the crista terminalis below the sinoatrial node region. Slices were cut tangential to the endocardium. The cutting chamber was filled with cold (4° C.) oxygenated (100% O2) modified Tyrode's solution (140 mM NaCl; 6 mM KCl; 10 mM glucose; 10 mM HEPES; 1 mM $MgCl_2$; 1.8 mM $CaCl_2$; 10 mM 2,3-butanedione monoxime (BDM), pH 7.4) with excitation contraction uncoupler 2,3-butanedione. The outer chamber is constantly refilled with ice to maintain constant 4° C. in the cutting chamber. The microtome was pre-set to 380 μm cutting thickness, 0.02-0.03 mm/s advance speed, 2 mm horizontal vibration amplitude, and 80 Hz vibration frequency. The microtome's z-axis vibration was also calibrated prior to each experiment with the ceramic cutting blade to <0.5 μm, which limited damage to a single layer of cardiomyocytes during the cutting procedure. After each slice was cut, they were transferred immediately to oxygenated (100% $O_2$) washout solution at 20° C. (modified Tyrode's solution: 140 mM NaCl; 4.5 mM KCl; 10 mM glucose; 10 mM HEPES; 1 mM $MgCl_2$; 1.8 mM $CaCl_2$; 1% Penicillin-Streptomycin; pH 7.4). Slices were placed in 100 μm nylon mesh cell strainers in 6 well plates with a bottom drilled through for oxygenation. A meshed washer was placed on top of the slice to prevent the tissue from curling. The tissue slices were kept in the washing solution for 20 minutes to washout the BDM and warm the tissue gradually to room temperature prior to transferring to culture device.

b. Culture device

Figure 7:
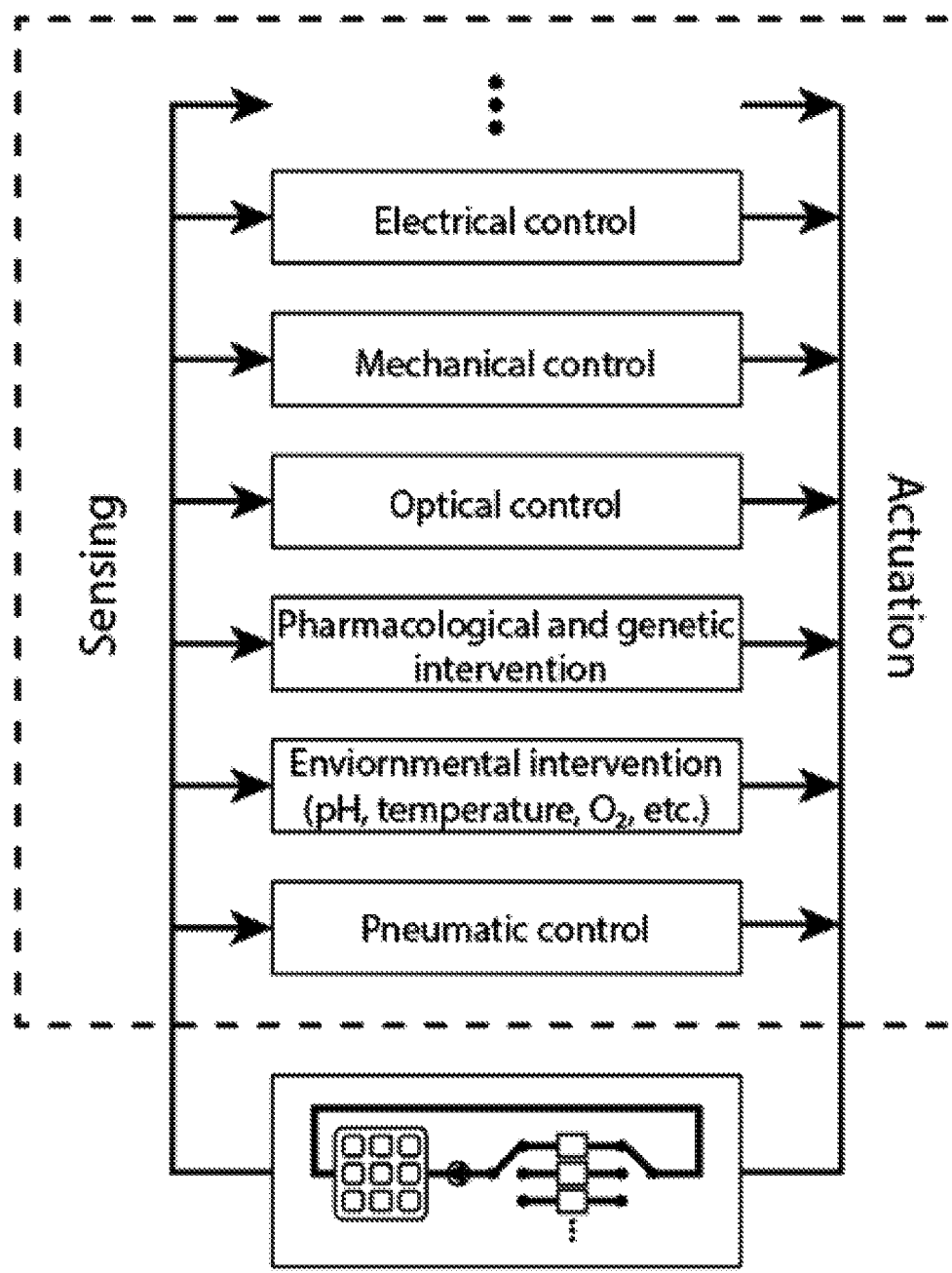
Figure 8:
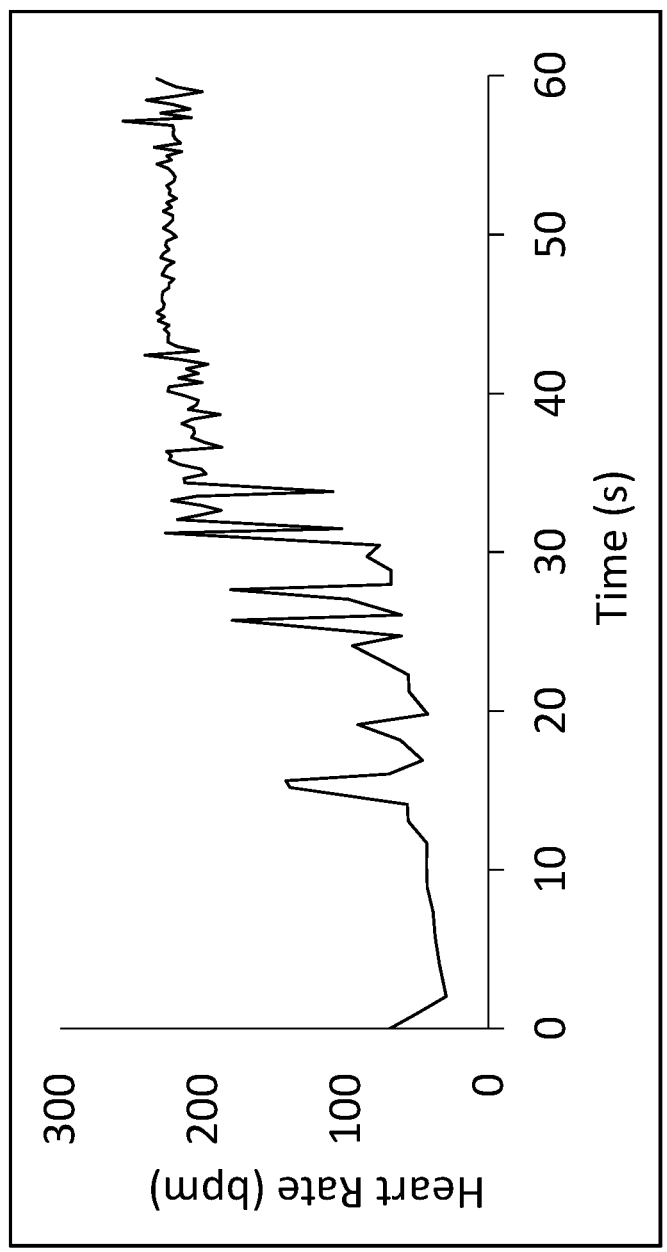
FIGS. 8 and 9 show that oxygenation and circulation of culture medium improve tissue viability.
Figure 9:
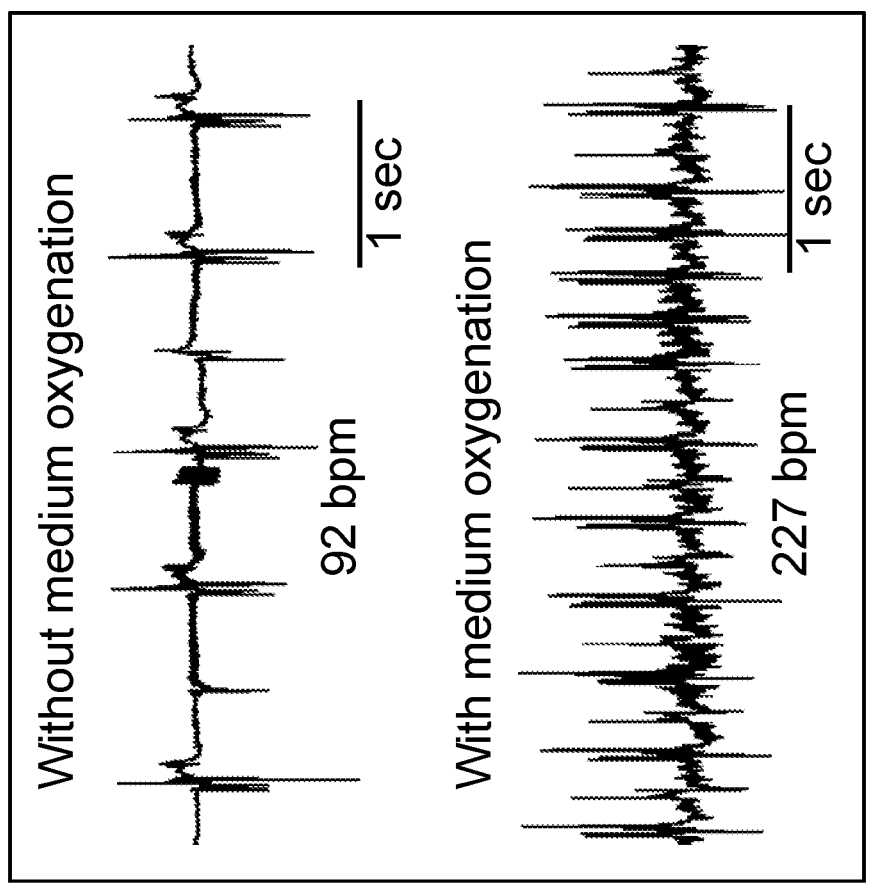

Without electrical and mechanical stimulation, long-term in vitro culture of cardiac slices is not viable due to tissue remodeling. An organotypic slice culture system with electrical, mechanical, and metabolic support can be developed using PDMS microfluidic fabrication techniques. A microcontroller is used to control and monitor components of the culture system (FIG. 3). The culture system maintains slice viability with electrical stimulation, mechanical loading and stimulation, media oxygenation, media circulation, and temperature regulation (FIGS. 6-7). For real-time monitoring and recording of functional, metabolic, transcriptional, and other physiological parameters of the tissue slices in culture, the culture system also consists of electrode arrays, force transducers, pH sensors, photodiodes, temperature sensor, oxygen sensor and other sensors (FIGS. 7-10). The culture system is completely self-contained and is capable of operating independently or carrying out user specified commands. The culture system interfaces with a central control unit via a wireless or wired communication. The central control unit has the ability to monitor and control multiple culture systems for high-throughput studies. Each culture system can interpret physiological measurements of the tissue slices based on readouts from the plurality of sensors for self-testing and data analysis. The central control unit can compare and analyze physiological measurements from multiple culture systems for high scalability.

For metabolic support, multiple micro-pumps, which include but are not limited to piezoelectric diaphragm pumps, gear pumps, centrifugal pumps and peristaltic pumps, are controlled by the microcontroller on the culture system for injecting purified air into the culture medium and to drive the flow of the culture medium inside the microfluidic culture chamber (FIGS. 3-4). With oxygen, flow, and temperature sensors, a feedback control mechanism is implemented to maintain the appropriate oxygen concentration, pH, flow rate, and temperature of the culture medium (FIGS. 6-7 and 10). Culture chambers housing the tissue slices are fabricated using a plurality of methods including but not limited to milling, casting, and 3D printing. For precise liquid handling for drug delivery, microfluidic micro-channel and on-chip valves are implemented. The chambers are linked with the microfluidic channels in series (FIG. 5A) and/or in parallel (FIG. 5B) or any combinations (FIG. 5C-D) depending on the design of the study. The culture system handles a plurality of solutions including culture medium, disinfectants, dissolved compounds, virus (e.g., a therapeutic virus) preparations, cell suspensions, and biomaterials. Flow valves are also incorporated into the culture system to control solution flow from and into multiple reservoirs for medium change and waste collection. To minimize contamination, the culture system flushes tissue slices with sterilized physiologically balanced solutions such as phosphate-buffered saline and/or culture medium after the slices are initially loaded into the culture chambers and periodically during culture.

To provide mechanical support and stimulation, each chamber contains multiple anchoring points where a flexible and stretchable substrate (e.g., a polydimethylsiloxane (PDMS) substrate) adhered to the tissue slice is attached to. For ease of operation, a quick release clamping mechanism is implemented to quickly open and close the tissue chambers for preventing damaging the tissue slices during loading.

Example 2

Methods and Systems for Organotypic Tissue Slice Culture a. Collection of Human Heart Experimental protocols described in this section were performed in accordance with all human research guidelines. Adult human hearts were procured as human donor hearts rejected for organ transplantation. Consents were obtained either from donors as previously granted or from family members allowing use of the hearts for research purpose. Following aortic cross-clamp, the hearts were cardioplegically arrested using University of Wisconsin (UW) solution (ViaSpan) in the operating room. The hearts were transported in the UW solution on ice.

b. Slice Preparation and Culturing

The procedures for slice preparation and culturing were described previously in detail (Kang, C. et al., Sci. Rep. 6:28798 (2016)). A sample approximately 1 cm×1 cm×1 cm was cut from the left ventricular (LV) free wall. Care was taken to ensure that the tissue was submerged in solutions at all times. The tissue samples were mounted onto the tissue holder of a vibrating microtome (Campden Instruments, UK) and sectioned into 380 μm thick slices while submerged in a modified Tyrode's solution (140 mM NaCl, 6 mM KCl, 10 mM Glucose, 10 mM HEPES, 1 mM $MgCl_2$, 1.8 mM $CaCl_2$, 10 mM BDM, pH 7.4). The cutting chamber was surrounded by ice to maintain a stable low temperature. The vibrating microtome was set to 0.4 mm/s advance speed, 2 mm horizontal vibration amplitude at 80 Hz. To minimize trauma to the tissue during sectioning, the undesired vertical vibration of the blade was laser-calibrated to less than 0.5 μm. After sectioning, each slice was placed in a cell strainer, weighed down with a meshed ring, and transferred to a bath of modified Tyrode's washout solution (140 mM NaCl, 4.5 mM KCl, 10 mM Glucose, 10 mM HEPES, 1 mM $MgCl_2$, 1.8 mM $CaCl_2$, pH 7.4). The slices were kept in the washout solution at room temperature (i.e., approximately 25° C.) for 20 minutes before optical mapping or culturing to washout BDM and reduce temperature shock.

c. Collection of Murine Heart and Isolated Atrial Preparation

Mice were anesthetized in accordance with IACUC animal research guidelines. Following loss of withdraw reflex, thoracotomy was performed to excise the heart. The excised heart was placed in oxygenated Tyrode's solution with pH adjusted to 7.4 at 37° C. With the posterior side of the heart facing up, a cut was made slightly above the midsection of the heart to remove the ventricles. Facing the same orientation, an incision from the tricuspid valve to the superior vena cava along the atrial septum was made under a surgical microscope. Subsequently, a portion of the atrial septum was removed to open the left atria. The edges of the atria were slightly stretched and pinned with the endocardial surface up. The resulting isolated atrial preparation preserved the intact SAN region, delimited by the crista terminalis, atrial septum, and orifice of the superior vena cava.

d. Culture of Cardiac Slices in an Incubator

To prevent contamination, cardiac slices were rinsed three times in sterile phosphate buffered saline (PBS) before culturing. The forceps used to handle the slices were sterilized with a bead sterilizer between each rinse. The slice culture medium consisted of Medium 199, 1×ITS, and 2% penicillin streptomycin. The slices were cultured in 6-well plates with one slice in each well and 3 mL of the culture medium. To facilitate oxygen diffusion into the slices, the plates were agitated on an orbital shaker at 20 rpm placed inside a tri-gas incubator (Thermo Fisher Scientific, Waltham, MA) with 30% $O_2$ and 5% $CO_2$ at 37° C. The culture medium was changed every two days.

e. Microcontroller-Controlled Tissue Slice Culture System

Custom electromechanical components were developed and fabricated to monitor and control the fundamental culture conditions, including media circulation, temperature adjustment, medium oxygenation, electrical stimulation, optical stimulation, and ECG recording. A microcontroller (Teensy 3.2, PJRC, Sherwood, OR) was used to monitor and actively control each component of the system. The microcontroller interfaced with the rest of the system via a custom breakout board. To achieve medium circulation, a peristaltic pump was prototyped using 3D printing technique to achieve the appropriate flow rate with low power consumption. To maintain medium temperature and oxygenation, a gas-exchanger was fabricated with built in thermofoil heater (Minco, Minneapolis, MN) using a 3-axis CNC mill (Roland DGA, Irvine, CA). Since a 5.5 V battery was used to power the entire system, a voltage boost regulator (LMR62010, Texas Instrument, Dallas, TX) was used to drive the heater at 12V. A gas permeable PDMS sheet separated the oxygen from the culture medium. A humidity and temperature sensor (HTU21D, SparkFun, Boulder, CO) was mounted onto the thermofoil heater to prevent overheating of the culture medium and to detect system leakage.

Each tissue chamber is instrumented with an array of sensors and actuators to monitor the culture condition and stimulate the tissue to minimize dedifferentiation. To monitor the temperature inside the culture chambers, a high-precision platinum temperature sensor (Digikey, Thief River Falls, MN) was embedded into each chamber. The temperature signal was digitized by a high-precision analog-to-digital converter (ADS1220, Texas Instrument, Dallas, TX) and recorded by the microcontroller. Using the culture chamber temperature, a negative feedback control loop is used to control the heaters to actively maintain a stable culture medium temperature. To record far-field pseudo ECG of cultured tissue, silver/silver chloride sensing electrodes were fabricated into the culture chambers. The pseudo ECG was amplified 1000 times with an operational amplifier, and digitized via a multichannel high sampling rate analog-to-digital converter (ADS131A04, Texas Instrument, Dallas, TX). The ECG data was recorded by the microcontroller at 2 kHz sampling rate for further processing. Electrical stimulation of the slices is achieved with field stimulation via platinum/iridium electrodes. For optical stimulation of the cultured optogenetic tissue, a 470±10 nm LED (Wurth Electronics, Niedernhall, Germany) was built into each well. All mechanical components were designed in AutoCAD and fabricated with a 3D printer, a laser cutter, and a 3-axis CNC mill.

Example 3

Long-Term Culture of Cardiac Slices in a Heart-on-a-Chip System

Using the protocol of Kang, C. et al. (Sci. Rep. 6:28798 (2016)), viable human cardiac slices were obtained from non-failing donor hearts that were rejected for transplantation and from end-stage failing hearts. Culture conditions were optimized to extend viability length of the cardiac slices in vitro. Using optical mapping, the conduction parameters of the culture cardiac slices were evaluated. To achieve long-term culture of human cardiac slices, an automated heart-on-a-chip system for organotypic culture of cardiac slices was developed and optimized using the microcontroller-controlled tissue slice culture system described in Example 2. The heart-on-a-chip system supports electrical stimulation to minimize tissue dedifferentiation. The system is also entirely self-contained to allow for shipping of live human cardiac tissue.

a. Long-Term Culture of Human Cardiac Slices

Extending the culture length of the cardiac slices while preserving the mature phenotype would enable the study of human cardiac physiology and the test of chronic pharmacological perturbation and gene therapies. Without microvasculature perfusion, the cardiac slices rely entirely on passive diffusion of oxygen and nutrients. At 380 μm, the thickness of the slices approaches the diffusion limit of oxygen in soft tissue (Barclay, C. J., J. Muscle Res. Cell Motil. 26(4-5):225-35 (2005)). Cardiac slices have previously been cultured on a liquid air interface to facilitate oxygenation of the slices and were able to preserve normal electrophysiology for two days (Kang, C. et al., Sci. Rep. 6:28798 (2016)). The culture protocol was modified to increase oxygenation of the liquid culture medium. A tri-gas incubator with 30% O2, 5% CO2 at 37° C. was used to culture the slices. The slices were individually cultured in 6 well plates with 3 mL of medium in each well. The culture plates were placed on an orbital shaker set at 20 rpm to further increase the dissolved oxygen concentration in the liquid culture medium.

Figure 11:
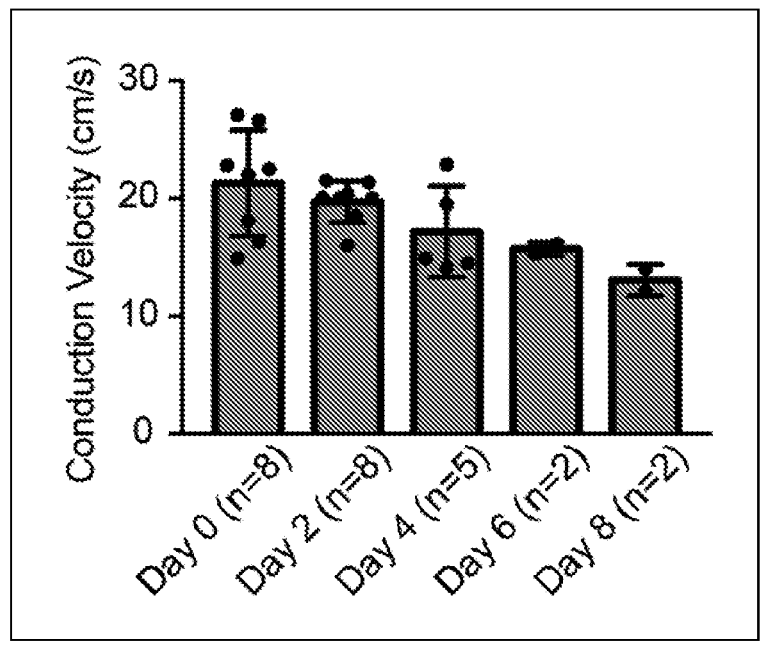
Figure 12:
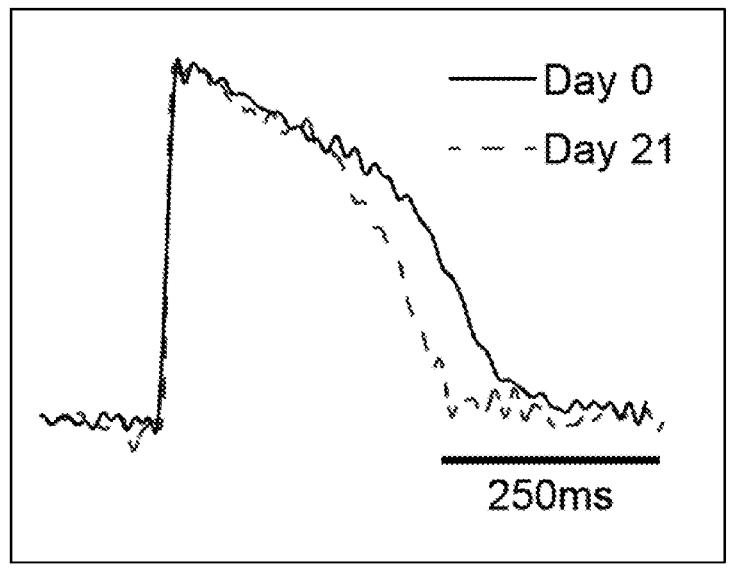

Surprisingly, human cardiac slices obtained from the left ventricular free wall unexpectedly remained electrically viable for up to 21 days in vitro and unexpectedly maintained normal electrophysiology for up to 4 days, as shown in FIGS. 11-13. Optical mapping was performed to measure the conduction parameters of the cardiac slices.

Optical mapping was achieved using a CMOS camera imaging system (ULTIMA-L, SciMedia, Costa Mesa, CA) to measure changes in transmembrane potential in acutely isolated and cultured murine atria and human slices. Both types of tissue were superfused in Tyrode's washout solution at 37° C. with the pH maintained at 7.4. To eliminate motion artifacts in the recorded optical signal, the isolated atrial tissue was immobilized using the excitation-contraction uncoupling agent, blebbistatin (10 μM), which has been shown to have no significant effects in action potential (AP) morphology. Subsequently, the tissue was stained via superfusion with a voltage-sensitive dye, Di-4-ANEPPS (61010, Biotium, Fremont, CA). A green LED light source (Prizmatix, Southfield, MI) with the wavelengths of 520±45 nm was used to excite the voltage-sensitive dye. The emitted fluorescence was filtered by a long-pass filter at 650 nm and collected by the ULTIMA-L camera as previously described (Kang, C. et al., Sci. Rep. 6:28798 (2016)).

Figure 2:
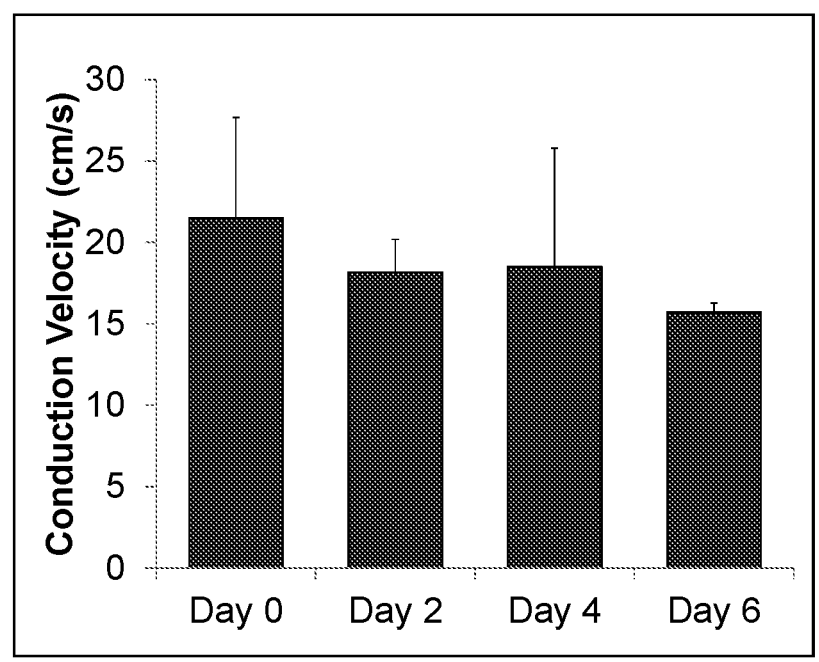

The recorded data was first visualized using Brainvision software and then analyzed using Rhythm, our open source custom developed MATLAB program (Laughner, J. I. et al., Am. J. Physiol. Heart Circ. Physiol. 303(7):H753-65 (2012), which is incorporated herein by reference in its entirety). The optical action potential signal was filtered with a 100 Hz low-pass filter, 3×3 binning, and a $1^{st}$ order drift correction. Activation maps of the isolated atrial tissues were generated based on the maximum derivatives of the optical signals ($dVm/dt_{max}$) (FIGS. 1, 13, and 24). Activation maps of the human tissue paced at a cycle length of 1000 ms were used to calculate the conduction velocity (FIGS. 2 and 11). Action potential duration was calculated by measuring the time elapsed between depolarization and 80% of repolarization (FIG. 12). The conduction velocity (CV) was measured at 1 Hz pacing.

Figure 13A:
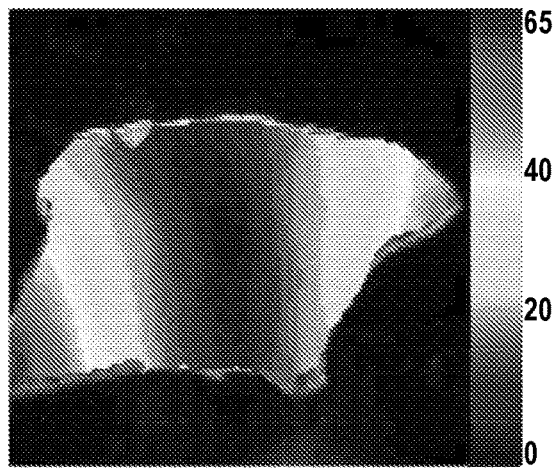
FIG. 13A shows an activation map of the fresh human cardiac slice.
Figure 13B:
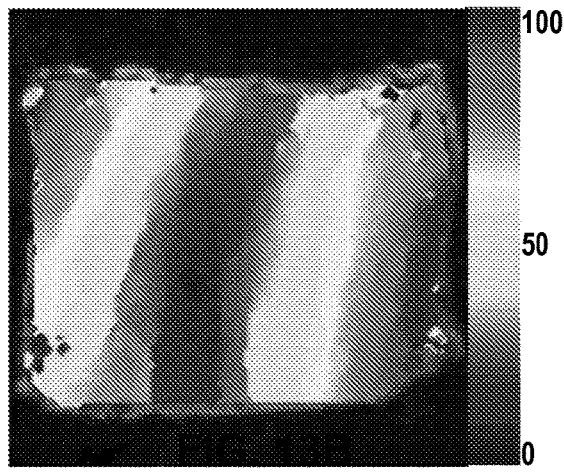
FIG. 13B shows an activation map of the human cardiac slice cultured for 21 days ("Day 21"). The bars adjacent to the activation maps of FIGS. 13A and 13B represent activation times in milliseconds (ms).
Figure 13C:
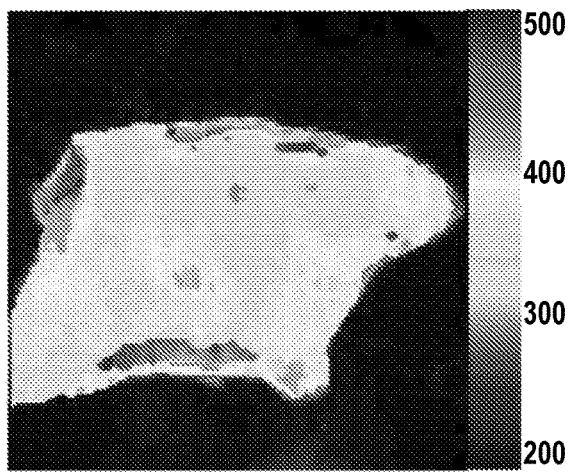
FIG. 13C shows an action potential duration (APD) map of the human cardiac slice shown in FIG. 13A.
Figure 13D:
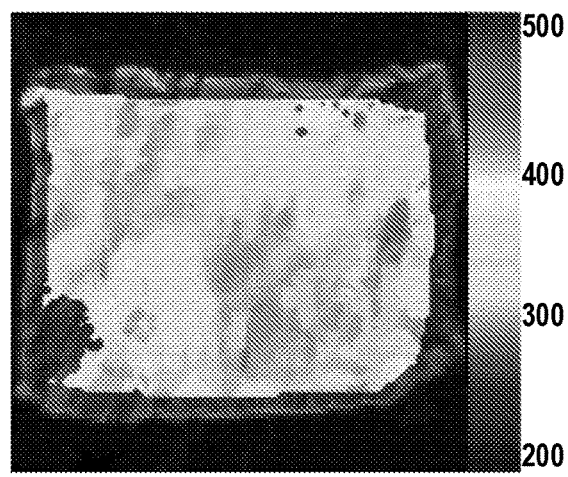
FIG. 13D shows an APD map of the human cardiac slice shown in FIG. 13B.

When compared with fresh slices, the cultured slices maintained anisotropic conduction (FIG. 13B), and uniform repolarization across the entire slice (FIG. 13D). The slices demonstrated preserved physiological conduction velocity for 4 days in culture (Day 0: 21.3±4.5 cm/s, Day 2: 19.7±1.8 cm/s, Day 4: 17.2±1.7 cm/s, Day 0 vs. Day 2: p=0.76, Day 0 vs. Day 4: p=0.14), as shown in FIG. 11. However, a significant reduction in CV was observed in the slices cultured for 21 days (6.7 cm/s). The slowed conduction in the long-term slice culture may be a manifestation of tissue remodeling and dedifferentiation due to the lack of electrical and mechanical loading.

b. Heart-on-a-Chip System

To prolong the culture period of human cardiac slices and prevent tissue dedifferentiation, a heart-on-a-chip electronic and microfluidic culture system was developed for organotypic culture of human cardiac slices in vitro, as shown in FIGS. 14-16. The heart-on-a-chip culture system, which was developed and optimized using the microcontroller-controlled tissue slice culture system described in Example 2, continuously monitors and maintains stable culture conditions, including culture medium temperature, circulation, and oxygenation. The culture chambers include actuators and sensors for electrical stimulation, sensing, and optical stimulation. Unlike cell lines that could be cryopreserved for shipping, live human cardiac slices are susceptible to hypoxia when not maintained properly, thus complicating shipping of live slices across the country or internationally. The culture system is also fully self-contained with integrated power supply, oxygen source, and media reservoir, allowing the maintenance of tissue viability during transportation. To increase culture capacity and reduce the cost of repair, the culture system is designed to be modular for plug and play operation.

The culture conditions inside the heart-on-a-chip system are closely monitored and adjusted by an array of sensors and actuators controlled by a microcontroller, as shown in FIG. 14. The system includes a custom control module, multiple culture chambers, pumps, heaters, a gas exchanger, a culture medium reservoir, a gas pressure regulator, and an oxygen tank. With an average current draw of below 600 mA, the culture system has an operation time of three days on a single portable 40,000 mAh battery, which is sufficient for over-night shipping. All culture parameters can be independently adjusted in real time to determine and maintain the optimal culture condition for human cardiac slices.

c. Smart Tissue Culture Chamber

Figure 18:
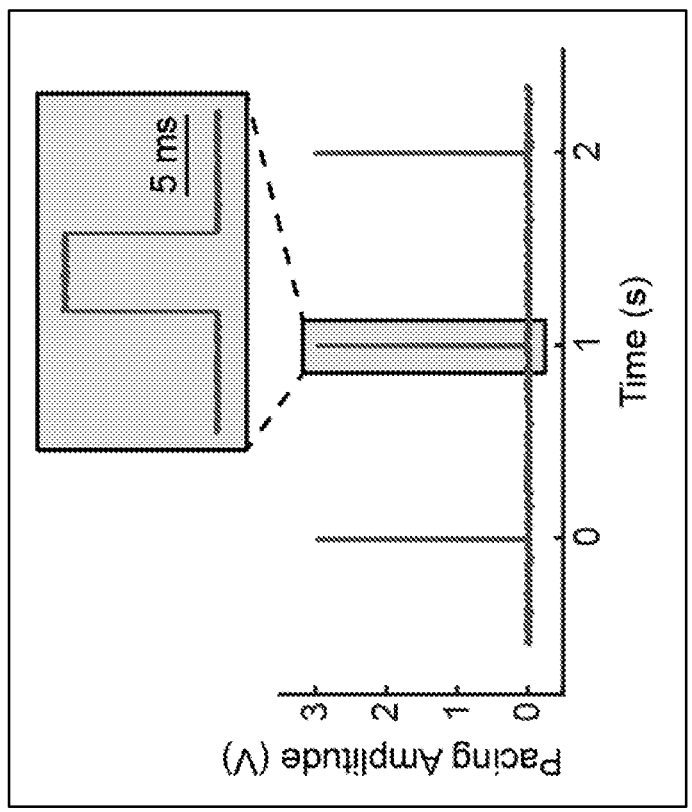
FIG. 18 shows a recoded waveform during electrical field stimulation with 3V pulse amplitude, 5 ms pulse duration, and 1 second pacing cycle length.

Electrical stimulation has been shown to maintain the structural and functional properties of isolated adult rat ventricular myocytes (Berger, H. J. et al., Am. J. Physiol. 266 (1 Pt 2):H341-9 (1994); Folliguet, T. A. et al., J. Thorac. Cardiovasc. Surg. 121(3):510-9 (2001), each of which is incorporated herein by reference in its entirety). To minimize tissue dedifferentiation and to monitor the culture parameters, culture chambers of the heart-on-a-chip culture system are instrumented with an array of actuators and sensors, including field-pacing electrodes, sensing electrodes, a temperature sensor, and a light source for optogenetic stimulation and fluorescence recordings (FIG. 16C). The chamber bottoms are coated with polydimethylsiloxane (PDMS) for mechanical anchoring of the slices using miniature dissection pins. To avoid physical damage to the slice from point pacing electrodes, platinum-iridium (Pt/Ir) electrodes, which have proven biocompatibility and low electrical resistance, are fabricated into the culture chamber for field stimulation. The default stimulation parameters are set at 3V pulse amplitude, 2 ms pulse duration, and 1 second pacing cycle length. As shown in FIG. 18, no undesirable voltage fluctuations were observed in the recorded stimulation waveform. The pacing parameters are user or software adjustable to allow for optimization of the pacing protocol during culture in case of changes in pacing threshold or specific protocol requirements.

Temperature of the culture medium is maintained by a feedback control system based on the temperature inside the chamber via a platinum resistance thermometer. Based on platinum's linear resistance-temperature relationship, an analog temperature signal is obtained by comparing the voltage from the platinum thermometer to a reference voltage with an instrumentation amplifier. The analog signal is then digitized with an analog to digital converter before being recorded and converted to Celsius by the microcontroller. Two configurations of the culture chambers are shown in FIG. 16B and FIG. 17. While both configurations perform similarly, the design shown in FIG. 16B is much more compact, with all electronic components integrated onto the same printed circuit board, whereas the system in FIG. 17 utilizes a modular design for the ease of scaling up culture capacity with plug and play operation.

Due to the scarcity of human heart tissue, isolated murine atrial preparation containing sinus node was used to test and optimize the culture system during development. Viability of the culture murine atrial preparation was measured by the intrinsic heart rate of the sinus node. To monitor the murine atrial sinus rhythm in culture, Pt/Ir sensing electrodes were fabricated into the culture chambers for pseudo ECG recording. The pseudo ECG was amplified 1,000× with an operational amplifier and digitized via a multichannel high sampling rate analog-to-digital at 2 kHz sampling rate. The ECG data was recorded by the microcontroller for post processing.

d. Custom Gas Exchanger

Figure 23:
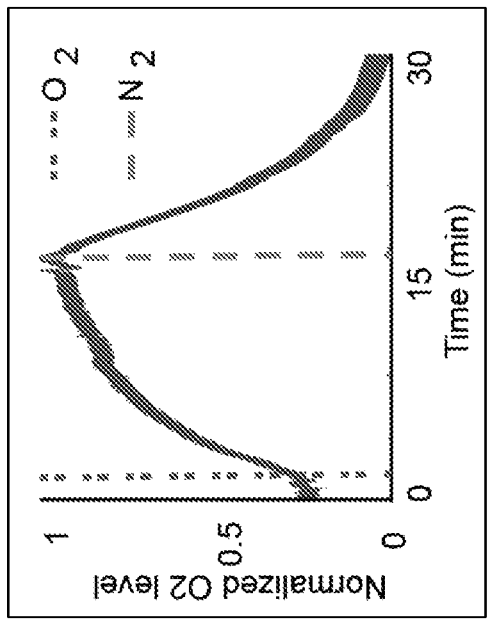

Since the thickness of human cardiac slices approaches the limit of oxygen diffusion, sufficient oxygenation of the culture medium is critical to maintaining tissue viability (Barclay, C. J., J. Muscle Res. Cell Motil. 26(4-5):225-35 (2005)). When cultured in a regular incubator with 20% O2, the core of the tissue slice may experience hypoxia, causing altered gene expression and reducing tissue viability (Giordano, F. J., J. Clin. Invest. 115(3):500-8 (2005); Huang, Y., FASEB J. 18(10):1138-40 (2004), each of which is incorporated herein by reference in its entirety). To supply sufficient oxygen to the slices, a custom gas exchanger was developed for the heart-on-a-chip culture system to oxygenate the culture medium before it is circulated to the culture chambers, as shown in FIG. 19. The gas exchanger contains two mirrored chambers separated by a 0.35 mm thick gas-permeable PDMS membrane. One chamber of the gas exchanger is pressurized with pure oxygen at 15 psi, while the culture medium flows through the mirrored chamber. The total oxygen exchange surface is 17 cm$^2$. Using an oxygen sensor (ADInstruments, Colorado Springs, CO), a dissolved oxygen concentration of 1.3 mM was measured in the culture medium, 5-6 times higher than that of conventional culture in a cell incubator (McMurtrey, R. J., Tissue Eng. Part C Methods 22(3):221-49 (2016), which is incorporated herein by reference in its entirety). As shown in FIG. 23, gas exchange occurs rapidly inside the culture system. When the gas exchanger was filled with pure oxygen, the diffused oxygen level reached saturation in approximately 15 minutes. Vice versa, when the oxygen was purged and nitrogen was fed into the gas exchanger, the oxygen concentration in the culture medium was depleted in approximately 15 minutes. To maintain tissue viability during transportation, the culture system also contains a portable small gas tank and a miniature pressure regulator (FIG. 21). The gas tank can be pressurized to 2100 psi, allowing for an estimated 3 weeks of oxygen supply.

e. Maintenance of Stable Culture Temperature

Since most enzymes denature rapidly at high temperatures and ion channel conductance is temperature dependent, the ability to maintain stable temperature inside the culture chambers is critical for preserving viability and normal electrophysiology of cardiac slices (Dumaine, R. et al., Circ. Res. 85(9):803-9 (1999); Milburn, T. et al., Receptors Channels 3(3):201-11 (1995); Voets, T. et al., Nature 430(7001):748-54 (2004), each of which is incorporated herein by reference in its entirety). A proportional control, a type of feedback control system, was implemented in the heart-on-a-chip culture system to maintain a stable culture medium temperature and to compensate for changing ambient temperature. Two thermofoil heaters were built into the gas exchanger and the medium reservoir, where the liquid medium has the greatest surface-to-volume ratio. Since heat transfer to the culture medium does not stop immediately when the heaters are powered off due to the large heat capacitance of the heaters, a proportional control system was implemented to avoid undesirable temperature fluctuations in the culture chambers, as shown in the following equation:

$$P_{out} = K_p e(t) + p0$$

Equation for proportional control, where p0 is output with zero error and is set at 37° C., e(t) is the instantaneous error at time t and is the difference between p0 and culture chamber temperature, $K_p$ is a proportional gain and is set at 1, $P_{out}$ is the target temperature of the heater. The upper limit of $P_{out}$ is set to 45° C. to avoid overheating of the culture medium.

Figure 22:
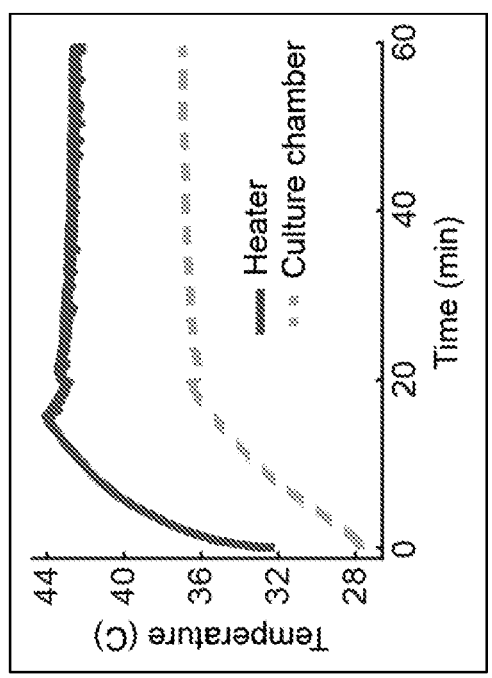

To prevent overheating of the culture medium, the temperature of the heaters is monitored and limited to a maximum of 45° C., well below the inactivation temperature of fetal bovine serum. As shown in FIG. 22, the culture medium inside the culture chamber reached 37° C. from room temperature within 20 minutes with minimal overshoot. The temperature was subsequently maintained without fluctuations.

f. Low-Power Pumps for Medium Circulation

Both heating and oxygenation of the culture media require circulation of the perfusion medium. A robust means of driving steady flow is critical for maintaining stable heat and gas exchange in the heart-on-a-chip culture system. Several pumps were evaluated for their long-term dependability and low power consumption, and a piezoelectric pump and a custom peristaltic pump were adopted for two different versions of the culture system. With a low power consumption of 250 mW, the piezoelectric pump is preferred when power is limited, such as during transportation of the culture system. However, since the piezoelectric pump works by rapidly deforming and releasing a piezo element when voltage is applied at a high frequency, the pump requires direct contact with the culture medium and can potentially increase the chance of contamination. For the long-term culture of the cardiac slices when the culture system is connected to an external power source, a custom 3D printed peristaltic pump, as shown in FIG. 20, was developed. Since the liquid is forced through a tube when compressed by rollers in a peristaltic pump, the tubing can be sterilized by ethylene oxide or autoclave to minimize the chance of contamination. With a power consumption of 1 W, the custom peristaltic pump is 10-15 times more power efficient than similar commercially available pumps. With built-in reduction gears, the peristaltic pump is also significantly more reliable than other low cost peristaltic pumps that drive the rollers via friction coupling. To avoid excess pressure buildup in the gas exchanger, the piezoelectric pump and the peristaltic pump are controlled by pulse width modulation to achieve a stable 2 mL/min flow rate.

g. Tissue Viability in the Heart-on-a-Chip System

Figure 24C:
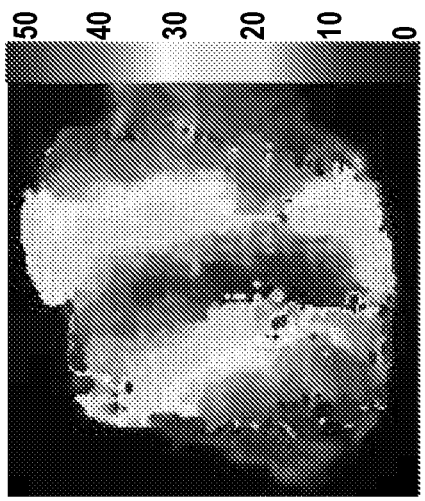
FIGS. 24A-C show activation maps of an acute human cardiac slice and slices cultured for 1 and 3 days in the culture system. The bars adjacent to the activation maps of FIGS. 24A-C represent activation times in milliseconds (ms).
Figure 24B:
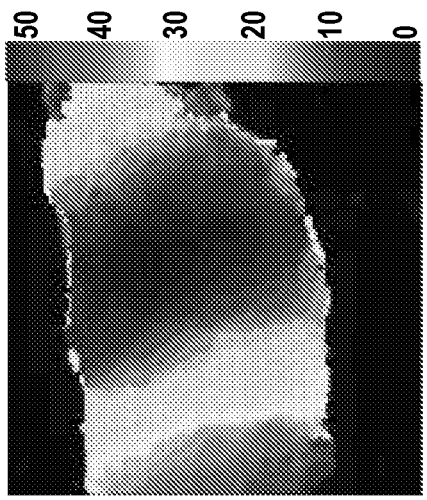
Figure 24A:
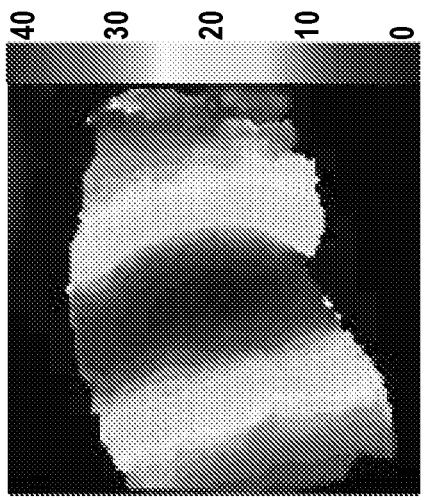
Figure 25:
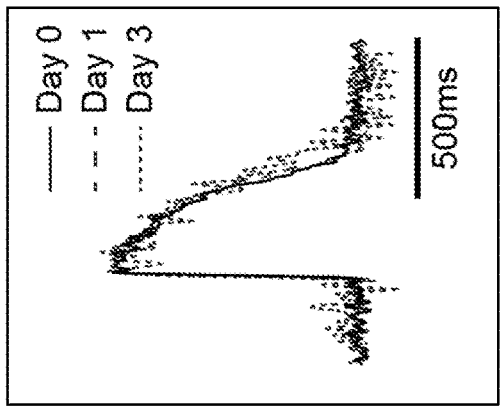

To evaluate the effectiveness of the culture system in maintaining viability of human cardiac slices, optical mapping of the cardiac slices cultured in the system was performed, and the automaticity of cultured murine atria was tracked. As a preliminary attempt to minimize tissue dedifferentiation, the human cardiac slices were paced at 1 Hz with 5 ms pulse width for 10 minutes every hour. As shown in FIG. 24, the human cardiac slices cultured in the heart-on-a-chip system remained electrically viable for up to 3 days. When compared with a freshly sectioned slice (FIG. 24A), the slices cultured for 1 day (FIG. 24B) and 3 days (FIG. 24C) demonstrated preserved anisotropic conduction and normal action potential morphology (FIG. 25). Greater noise was observed in the optical action potential recorded from the human cardiac slice cultured for 3 days, suggesting declining tissue viability. Medium flow rate, oxygenation, medium composition, and the electrical stimulation protocol are all easily adjustable with the culture system and can be optimized to achieve long-term culture of human cardiac slices.

Figure 26:
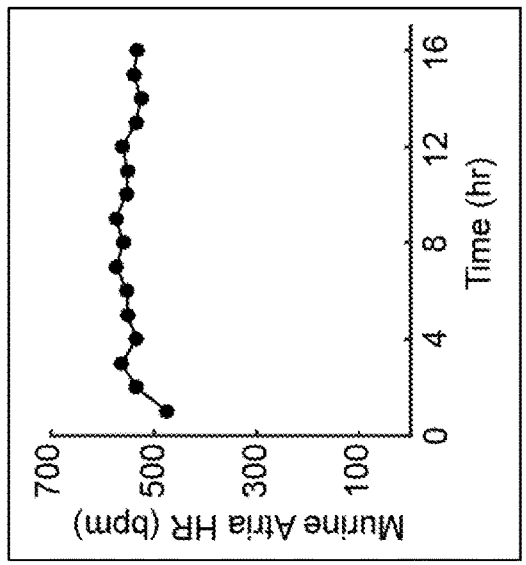
Figure 27:
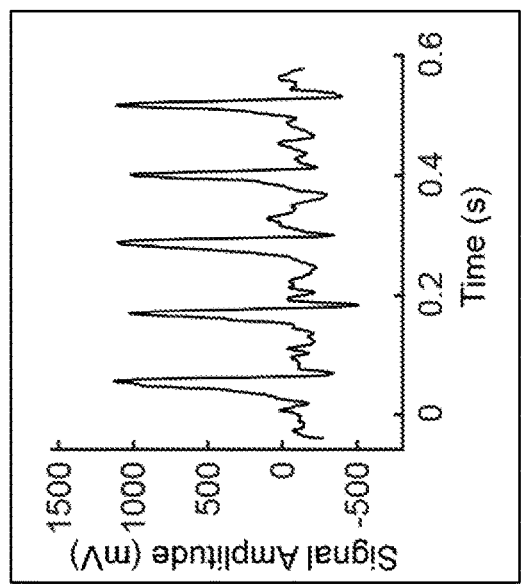

Isolated murine atrial preparation has been used to study atrial conduction and pacemaking (Choate, J. K. and Feldman, R., Am. J. Physiol. Heart Circ. Physiol. 285(3): H1340-6 (2003); Glukhov, A. V. et al., J. Mol. Cell. Cardiol. 48(1):152-60 (2010); Swaminathan, P. D. et al., J. Clin. Invest. 121(8):3277-88 (2011), each of which is incorporated herein by reference in its entirety). The preparation can also be maintained in culture for an extended period due to the thickness of the tissue. During development of the culture system, isolated murine atrial preparation was used to test the culture system. Since the sinoatrial node is preserved on the preparation, automaticity of the murine atria can be tracked as a measure of tissue viability. As shown in FIG. 26, the cultured murine atria exhibited stable physiological heart rate in the culture system. To reduce motion artifacts in the far-field electrical recording, the system was programmed to power down medium circulation and heating during recording. As shown in FIG. 27, a clean atrial electrical signal could be recorded for heart rate calculation.

Figure 28:
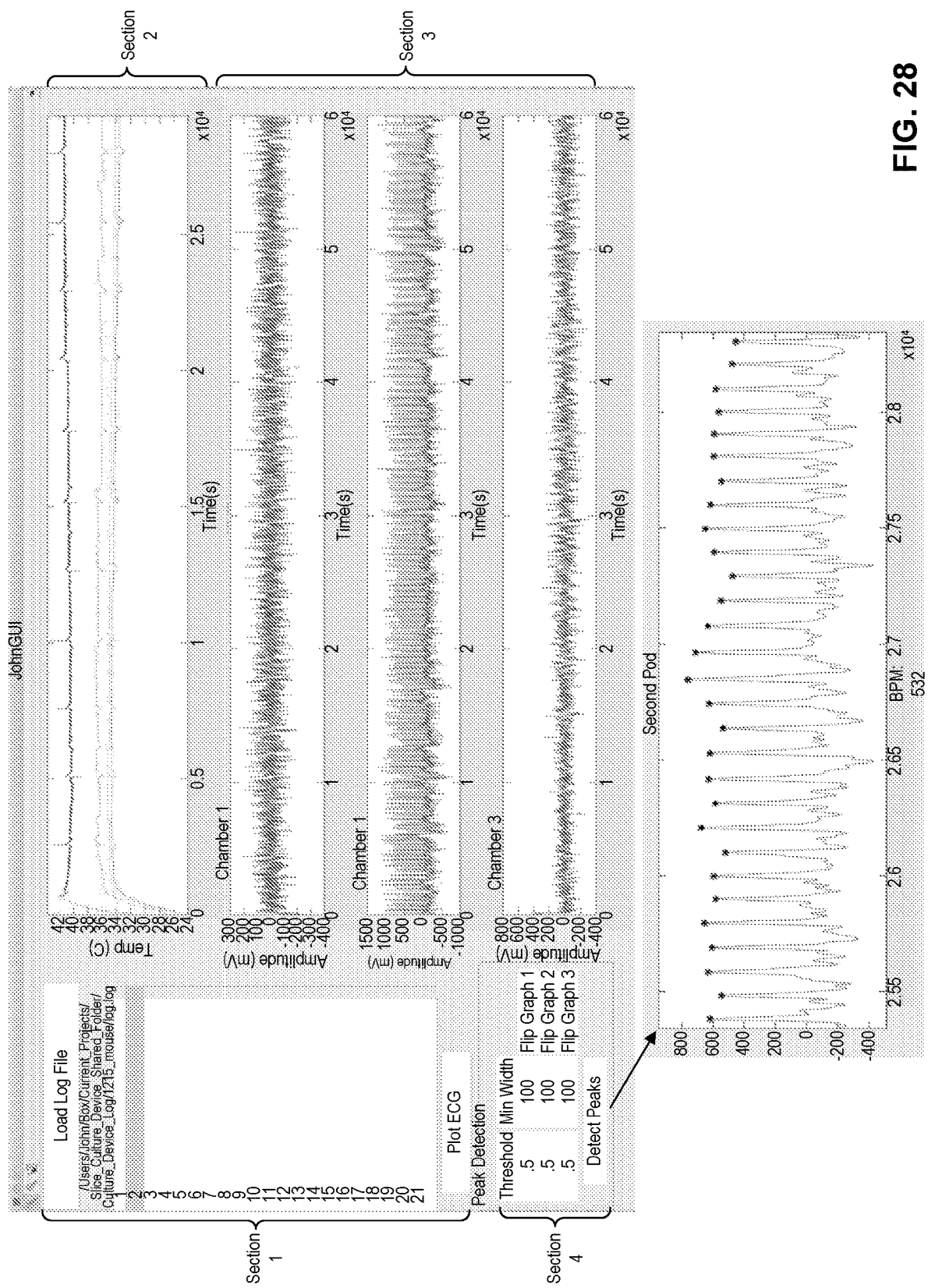
FIG. 28 depicts custom monitoring and analysis software. The main graphical user interface has 4 sections. Section 1 is for loading the device log and for selecting ECG recordings. Section 2 shows the history of the device temperature. Section 3 shows the pseudo-ECG recorded from the culture chambers. Section 4 is used for performing heart rate calculations with user selectable peak detection parameters.

A custom MATLAB program and a graphic user interface (GUI) were developed to monitor the performance of the culture chamber and the condition of culture murine atria, as shown in FIG. 28. Section 2 in the GUI shows the temperatures of the heaters and the culture chambers over time for tracking heater and pump malfunction. Section 3 shows far-field electrical recordings from the culture chambers. The recorded signal was filtered by a $2^{nd}$ order Butterworth notch filter to remove the 60 Hz power line interference and a $5^{th}$ order band-pass Butterworth filter with a lower cutoff frequency at 5 Hz and a higher cutoff frequency at 100 Hz to remove drift and additional noise in the signal. Peak detection with user selectable settings can be performed on the electrical recordings for heart rate calculation.

h. Discussion

Human cardiac slices are advantageous as a model for studying human cardiac physiology and for drug efficacy and toxicity testing (Kang et al., 2016). However, the limited culture duration and the intricate culture protocol impeded the use of human cardiac slices for long-term studies. The improved culturing methods and automated, self-contained heart-on-a-chip system disclosed herein maintain normal electrophysiology of the human cardiac slices long term, which is useful for transporting live tissue.

Several studies have demonstrated the feasibility of maintaining cardiac slice viability in culture, but have observed significant tissue remodeling in the slices cultured long term. In the absence of electrical and/or mechanical stimulations, cardiomyocytes undergo significant remodeling and dedifferentiation, evident by diminished contractile force, triangulation of action potential morphology, and reduced gap junction expression (Brandenburger, M. et al., Cardiovasc. Res. 93(1):50-9 (2012); Kaneko, M. et al., J. Cell Sci. Ther. 3(4):e1000126 (2012)). Using the methods disclosed herein, cultured human cardiac slices maintain normal electrophysiology for up to 4 days and remain electrically viable for up to 21 days when cultured inside a high oxygen environment. Significant reduction in CV was observed in the cardiac slices cultured longer than 4 days. The reduction in CV of the cultured slice was likely due to tissue dedifferentiation in the absence of electrical and mechanical stimulation. To overcome this, the heart-on-a-chip culture system was developed with electrical stimulation and mechanical anchoring capabilities as a platform to optimize organotypic culture of the human cardiac slices.

Optical mapping was utilized to characterize the conduction parameters of the cardiac slices at a high spatial and temporal resolution. Optical mapping is also capable of measuring other functional parameters such as the intracellular calcium and the metabolic state, using calcium-sensitive fluorescent dyes and NADH fluorescence (Lou, Q. et al., J. Vis. Exp. 55:e3160 (2011); Moreno, A. et al., Sci. Rep. 7:45744 (2017), each of which is incorporated herein by reference in its entirety). However, the use of fluorescent probes in optical mapping hampers its ability to take repeated measurements on the same slice over the length of culture. To overcome this, other techniques such as intracellular microelectrode recording and multi-electrode array recording can be applied to study the cardiac slices (Camelliti, P. et al., J. Mol. Cell. Cardiol. 51(3), 390-8 (2011)).

The prolonged culture of human cardiac slices demonstrated herein allows for the study of chronic drug effects, gene therapies, and gene editing. Adenoviral (Ad) vectors are a promising approach for in vivo gene delivery due to the ease of producing high titer as compared to lentivirus and the larger packaging capacity as compared to adeno-associated virus (Thomas, C. E. et al., Nat. Rev. Genet. 4(5):346-58 (2003), which is incorporated herein by reference in its entirety). However, the clinical adoption of Ad vectors for gene therapy has been limited by its dependence on the coxsackievirus and adenovirus receptor (CAR) for transduction (Dmitriev, I. et al., J. Virol. 72(12):9706-13 (1998), which is incorporated herein by reference in its entirety). With the preserved native extracellular matrix, the cardiac slices are a powerful platform for testing advancements in vector technology, such as tropism-modified CAR-independent Ad5 vectors.

With the prolonged culture length, human cardiac slices can be used as an accurate model of the human myocardium for testing the effect of exogenous gene expression. Optogenetic stimulation and inhibition with light-gated ion channels such as Channelrhodopsin-2 (ChR2) and anion channel rhodopsins (ACRs) has been proposed as a selective and safe method of cardiac pacing and cardioversion (Govorunova, E. G. et al., Science 349(6248):647-50 (2015); Jia, Z. et al., Circ. Arrhythm. Electrophysiol. 4(5):753-60 (2011), each of which is incorporated herein by reference in its entirety). With built-in LED light source and far field-sensing electrodes, the heart-on-a-chip culture system can perform automated evaluations of optogenetic stimulation on specific regions of the adult human heart. RNA interference (RNAi) has been proposed as a potential therapeutic and research tool. The ability to silence specific genes of interest with small interfering RNA (siRNA) and short hairpin RNA (shRNA) makes RNAi a powerful tool for studying cardiac physiology (Poller, W. et al., Cardiovasc. Res. 86(3):353-64 (2010); Suckau, L., et al., Circulation 119(9):1241-52 (2009), each of which is incorporated herein by reference in its entirety). The approach has been used for suppressing inflammatory response and oxidative stress to improve cardiac function following myocardial infarction in animal models (Hong, J. et al., Biomaterials 35(26):7562-73 (2014); Somasuntharam, I. et al., Biomaterials 34(31): 7790-8 (2013), each of which is incorporated herein by reference in its entirety). When applied to human cardiac slices, RNAi can be used to gain valuable insights to human cardiac physiology by selective knockdown of specific ion channels and subunits.

The heart-on-a-chip culture system was developed to achieve long-term culture of human cardiac slices while preserving normal physiology. The heart-on-a-chip system allows for the individual adjustment of different culture parameters and thus the establishment of the optimal culture condition. The heart-on-a-chip culture system was also designed to be entirely self-contained to support shipping of live cardiac slices. Using preset parameters and a feedback control system, the culture system maintains stable temperature, circulation, and oxygenation of the culture medium. The culture chambers are instrumented with an array of actuators and sensors for electrical stimulation, mechanical anchoring, electrical recording, and optogenetic stimulation and sensing.

Continual stimulation of isolated adult rat cardiomyocytes was found to preserve contractility, evident by the preserved amplitude of contraction, the velocities of shortening and relaxation, and the peak calcium current density (Berger, H. J. et al., Am. J. Physiol. 266(1 Pt 2):H341-9 (1994)). In the field of tissue engineering, electrical stimulation was also shown to improve expression of major cardiac markers and induced cell alignment and coupling in hiPSC-CMs (Radisic, M. et al., Proc. Natl. Acad. Sci. 101(52):18129-34 (2004), which is incorporated herein by reference in its entirety). With built-in field pacing electrodes, the heart-on-a-chip culture system allows for testing of electrical stimulation protocols with different frequencies and durations to establish the optimal protocol for minimizing tissue dedifferentiation. Pt/Ir was chosen as the material for the pacing electrodes to avoid release of free radicals that could cause oxidative stress to the tissue. Any proton gradient generated by the electrical field would be dissipated by the circulation of the culture medium. In extreme cases where continuous high frequency pacing might be required to maintain tissue phenotype, electrolysis of the culture medium would break down sodium chloride and water molecules to form sodium hydroxide, causing an increase in pH of the culture medium. The addition of a pH sensor would allow for real-time adjustment of the culture medium pH.

To maintain a stable temperature in the culture system, the effectiveness of three types of feedback control systems (i.e., on-off control, proportional control, and proportional-integral-derivative (PID) control) were evaluated. Also known as a hysteresis controller, an on-off controller rapidly switches the power state of the heaters based on the temperature inside the culture chambers and is the easiest to implement. However, the on-off controller does not compensate for the delayed heat exchange between the heaters and the culture medium, causing large temperature oscillations. On the other hand, a PID controller can achieve stable temperature control for a given system configuration when the proportion, integral, and derivative terms are well characterized. However, the stringency of a PID controller hinders its ability to adjust to changing system configurations. Therefore, the proportional controller was implemented in the heart-on-a-chip culture system to achieve a stable temperature while allowing for plug and play operation of the culture chambers when expanding the culture capacity.

As illustrated in FIG. 29, additional components for multiparametric functional characterization of cultured human cardiac slices can be implemented in the culture device to achieve automated testing of drugs, gene therapies, and gene editing. Examples of such components include, but are not limited to, a microelectrode array system for real-time monitoring of CV and APD and a compact optical detection system for measuring transmembrane potential, intracellular calcium dynamics, and metabolic function. The automated heart-on-a-chip platform with organotypic human cardiac slices is ideal for pre-clinical drug testing and research in human cardiac physiology. In addition, integration of heart-on-a-chip with other human organ tissue slices and/or human iPSC derived cell/tissues allows human-on-a-chip systems physiology investigations.

Example 3

Methods of Clinical Testing with Organotypic Human Tissue Slice Culture

Adult human tissue slices function as a tool to study fundamental human physiology as well as a preclinical screening platform for novel drug, gene, device, cell, tissue engineering, or other types of therapies. Sliced tissue is kept in the portable culture device to retain its electrical and mechanical properties. Therapy is delivered on to the slice tissue through perfusion. Mode of agent delivery is predicated by the type of therapy, and can be adapted for future trial therapeutic models.

In the past two and half decades of transgenic mouse studies, an enormous number of molecular targets have been determined to play a role in human diseases and arrhythmia. Under the current reductionist research paradigm for understanding and developing therapy for a particular disease, first, the clinical determinants of the disease are identified from patients. Second, specific symptoms of the disease are reproduced via genetic or procedurally reproduced in an animal model. Therapy or genes of interest are examined to identify a potential therapy in the animal model. Finally, the potential therapy is evaluated in clinical trials for safety and efficacy. Despite the sheer volume of discoveries in signaling pathways, gene functions, and normal and pathologic mechanisms are staggering, the impact of these data on human cardiovascular disease is humbling. In fact, these scientific understanding and advances have very rarely been translated to the bedside. It is painfully clear that understanding of molecular and functional mechanisms in a simpler organism such mouse or rat should not be taken as understanding of said mechanism in a far more complex model such as human.

While utilization of animal models cannot be discounted due to their flexibility and versatility, a pre-clinical trial human model would greatly improve the therapy translation from bench to bedside. In the past, no such model exists to study both the acute and chronic response to therapy. Two widely accepted human models are isolated primary cells and coronary/arterial perfused preparations. The former is susceptible to enzymatic damage during isolation, while the latter is resource and time consuming. Neither preparation can be maintained for more than a few hours. The slice model fills the gap between these two models.

a. Safety Testing of Various Drugs (e.g., Cardiotoxicity of Cancer Medications)

Tissue slices collected from adult organs is a valuable tool for testing efficacy and safety of various pharmacological compounds. A commonly used chemotherapeutic agent—doxorubicin (DOX), has been implicated to induce heart failure (HF) in patients. Various stress signaling pathways have been identified to play a crucial role in HF development and inhibition of various components of these signaling pathway has been determined to attenuate the effects of the drug in rodent models injected with DOX. However, it is not known if these effects translate to human hearts. Culturing of human cardiac slices treated with DOX allows the study of acute and chronic effects of DOX in HF development in humans. Specifically, slices will be prepared from human ventricles and electrophysiological parameters like conduction velocity and action potential parameters will be studied at 2 hours and at 2,4 and 6 days after DOX treatment by optical mapping. Additionally, microelectrode array mapping will be performed in DOX treated slices to determine the progression of DOX-induced HF in the same slice over 6 days. Finally, the benefits of inhibiting various components of the stress signaling pathways like the p38 MAPK isoforms by genetic and pharmacologic interventions will be determined in these slices.

b. Efficacy and Safety of Cardio-Active Drugs

Development of anti-arrhythmic drugs for the past several decades has been filled with disappointments. Except for Class II anti-arrhythmic drugs (beta-blockers), most other drugs have pro-arrhythmic tendencies. Repolarization is the critical factor in arrhythmia genesis and maintenance, contributing both to the trigger and substrate of the arrhythmia. Human repolarization is primarily governed by slow and fast rectifier currents, IKr and IKs. However, these channels are completely absent in a mouse model (Nerbonne, J. M. et al., Circ. Res. 89(11):944-56 (2001)). Mouse hearts, which beat at over 500 bpm, are naturally protected against all forms of arrhythmia unlike a human's heart which beats at a tenth of the rate. Therefore, in order to study arrhythmia in mouse models, drastic alteration to molecular signaling pathways and functional response are required to reproduce the phenotype in question.

Utilizing cultured slices and an adult dosage of phenylephrine, a widely used selective $\alpha_1$-adrenergic receptor agonist, a model to study chronic drug effects in human cardiac slices is developed. Slice electrophysiology was first acutely measured using optical mapping after application of 3 µM phenylephrine. Then acute slices were placed in either control culture which consist of medium 199, 2% penicillin-streptomycin, 1×ITS (Insulin, Transferrin, Selenium liquid media supplement, and 10 mM 2,3-butanedione monoxime or drug medium including 3 µM phenylephrine. Slices were cultured in a tissue incubator for 24 hours. Control cultured slices were measured before and after phenylephrine application similar to acute slices, slices cultured in drug media were measured separately. Two electrophysiology parameters are measured and substantial difference is found between acute and chronic stimulation modes.

c. Gene Therapy

Long-term culture of human tissue slices allows for evaluation of gene therapy in a human model system. Unlike human ventricular wedge preparations, tissue slices can be maintained for a prolonged period of time, which is required for viral transduction and tissue remodeling to occur in gene therapy. When compared with iPSC-derived cells and isolated primary cells, tissue slices preserve the natural multicellular environment and coupling with the surrounding myocytes, which are critical in evaluating the efficacy and safety of gene therapies.

A number of methods can be used to facilitate viral transduction in human tissue slices. The most common method is directly adding an appropriate number of viral particles in the culture media to achieve sufficient multiplicity of infection. As an alternative, microcapillary needles can be used to deliver therapeutic virus with high spatial specificity. To maximize viral transduction efficiency, enzymes such as collagenase and/or trypsin can be mixed with virus and added to tissue slices.

d. Gene Editing (e.g., TALENS, CRISPR/Cas9)

Since 2005, Genome-wide association studies (GWAS) have examined thousands of individuals for identification of single-nucleotide polymorphisms (SNPs) associated with major human diseases. Thousands of SNP associations have been found for hundreds of diseases and traits. With the development of highly specific gene modulation techniques such as TALENS and CRISPR/Cas9, SNPs identified by GWAS can now be validated and corrected in a human model system using tissue slices. For example, GWAS identified SNPs could be introduced to tissue slices obtained from healthy individuals to study the contribution of individual mutations in diseases. Vice versa, existing SNPs in tissue slices obtained from individuals with specific diseases could be corrected to study the efficacy of TALENS and CRISPR/Cas9 as methods for gene therapy.

e. Cell Therapy and Tissue Engineering

Cell therapy has been widely investigated as a therapeutic approach in regenerative medicine. Typically, either stem cells and/or cells derived from stem cells are introduced to a host for tissue regeneration. Different types of stems cells, such as embryonic stem cells (ESCs), induced pluripotent stem cells (iPSCs), and adult stem cells, have been studied in the context of cell therapy. However, each type of stem cell poses its own challenges when adapted for clinical applications. For instance, ESCs can develop into any organs in normal development, thus they are highly pluripotent and are ideal for tissue specific differentiation and regeneration. However, since human ESCs are obtained from in vitro fertilization, the use of ESCs in scientific research and clinical applications are limited due to regulatory and ethical issues. iPSCs are cells that have been genetically engineered to revert from tissue specific cells to a pluripotent, embryonic-like state. Since iPSCs can be created from cells obtained from a variety of sources such as skin biopsies, blood and urine samples, iPSCs have been the most widely used stem cell type in cell therapy for tissue specific cell differentiations. Despite its wide adaptation in cell therapy, studies have shown that iPSCs do not have the same degree of pluripotency as ESCs. Adult stem cells are tissue-specific stems cells that can be directly isolated from tissue biopsies without additional genetic modifications. However, these cells are multipotent, thus can only be used to derive cell types within their tissue of origin.

Cell type specific differentiation of stem cells is a complicated process. The organ on a chip system offers a platform for studying cellular and non-cellular communication of stem cells with their surrounding environment during differentiation. To study the effect of cellular communication on stem cell differentiation, stem cells are seeded on organotypic slices of different organs at different seeding densities. Non-cellular elements can also affect stem cell differentiation. Using the array of actuators described previously, non-cellular elements including but not limited to chemical composition of culture media, pH, and mechanical stimulation are altered in the organ on a chip system to study their effect on stem cell differentiation. The degree of differentiation of the stem cells is monitored by an array of sensors described previously. In addition to investigating stem cell differentiation, the organ on a chip system can also be used to test existing cell therapy solutions for efficacy and safety. Cells are labeled with fluorescent and/or non-fluorescent markers prior to seeding. By seeding different types of differentiated stem cells separately and/or together on organotypic slices of different organs, the lab on a chip system can monitor apoptosis of seeded cells, integration of the cells with host slices, and condition of slices undergoing cell therapy.

One of the major challenges in cell therapy is cell migration from site of delivery and lack of mechanical support. Significant effort has been invested in growing engineered cells in 3D constructs of various biomaterials to mimic native tissue. Demonstrating appropriate mechanical and electrical coupling between the 3D engineered tissue constructs and native organ is critical for proving efficacy and safety of engineered tissue constructs as a potential therapeutic approach in regenerative medicine. For instance, mismatch of mechanical and electrical properties between an engineered cardiac patch and the heart could lead to diminished cardiac output and susceptibility to arrhythmias. To study integration of 3D engineered tissue constructs with native tissue, tissue constructs of different materials seeded with different cells are grown on top of organotypic slices obtained from different organs. Mechanical and electrical coupling between the engineered constructs and organotypic slices will be evaluated using the array of actuators and sensors described previously.

f. Implantable Bioelectronics (e.g., Soft Electronics, Biodegradable Electronics)

Implantable devices are a critical component of disease therapy. They provide replacement and support for damaged physiological structure or function that cannot be treated via pharmacological intervention. Newer generation of implantable electronics requires thorough testing before surgical placement into the patient. Older devices which can only sense and actuate on one element of a disease and/or condition are no longer adequate. Increasing amount of study demonstrate the importance of understanding synchrony, and lack thereof, between electrophysiological, mechanical and metabolic elements.

For example, flexible and stretchable electronics which can adhere and move with native tissue, such as the "heart sock", provide high resolution multi-parametric mapping of both electrophysiology and metabolic parameters. Utilizing multi-dimensional data, a clinician can better assess the disease and provide patient specific therapy regimen. Furthermore, active electronics is also a major improvement over currently available devices. Capacitive electrode array can provide both sensing and actuation in a completely sealed device. This dramatically reduces current leakage and prolongs device life span. Moreover, biodegradable devices open much more possibility in medical device design. This technology eliminates the need for additional surgery to remove the device when it becomes unnecessary or unsuitable. All these cutting-edge technologies in device design can be tested in the organotypic human tissue slice culture device.

The breadth and scope of the present invention should not be limited by any of the above-described exemplary embodiments, but should be defined only in accordance with the following claims and their equivalents.

What is claimed is:

1. A method for maintaining a cardiac tissue slice in a microfluidic device, the method comprising culturing the cardiac tissue slice in the microfluidic device, wherein the microfluidic device comprises:
   (a) a tissue culture chamber that houses the cardiac tissue slice, wherein the tissue culture chamber provides a restricted environment supplied with oxygen and nutrients necessary to maintain a desired phenotype for the cardiac tissue slice;
   (b) actuators for minimizing remodeling and dedifferentiation of the cardiac tissue slice and for phenotypic interrogation of the cardiac tissue slice, wherein the actuators comprise an electrical stimulator and a mechanical stimulator;
   (c) one or more sensors for measuring one or more physiological parameters of the cardiac tissue slice; and
   (d) an electronics module comprising a microcontroller, wherein the electronics module is coupled to the actuators and the one or more sensors by an array of electrodes,
   wherein the desired phenotype of the cardiac tissue slice is maintained in the tissue culture chamber by: (1) electrically and mechanically stimulating the cardiac tissue slice with the electrical and mechanical stimulators, respectively, (2) measuring the one or more physiological parameters of the cardiac tissue slice with the one or more sensors, (3) analyzing the phenotype of the cardiac tissue slice, and (4) electrically and mechanically stimulating the cardiac tissue slice with the electrical and mechanical stimulators, respectively, to minimize remodeling and dedifferentiation of the cardiac tissue slice.

2. The method of claim 1, wherein:
   (a) the actuators further comprise a chemical stimulator, an optical stimulator, or a combination thereof,
   (b) the one or more sensors comprise a temperature sensor, an oxygen sensor, a pH sensor, a humidity sensor, one or an array of photodetectors, a force transducer, an electrical sensor, or a combination thereof, or
   (c) a combination thereof.

3. The method of claim 1, wherein the microfluidic device further comprises:
   (a) a central control unit, wherein the central control unit is coupled to the microcontroller, and wherein the central control unit is configured to analyze data from the one or more sensors,
   (b) a media reservoir, wherein media enters the tissue culture chamber through an inlet and exits the tissue culture chamber through an outlet,
   (c) an oxygen tank, a gas exchanger, and a heater, or
   (d) a combination thereof.

4. The method of claim 1, wherein the mechanical stimulator comprises a mechanical loading pole that secures the cardiac tissue slice within the tissue culture chamber and provides mechanical stimulation to the cardiac tissue slice.

5. The method of claim 1, wherein the microfluidic device is a self-contained culture system designed for long-distance transportation, wherein the self-contained culture system comprises an integrated power supply, an oxygen tank, a gas exchanger, a heater, a pump, and a media reservoir, and wherein the self-contained culture system maintains viability of the cardiac tissue slice during long-distance transportation by providing optimal medium circulation, oxygenation, temperature control, and stimulation.

6. The method of claim 1, further comprising inducing cardiac dysfunction by chronic pathological stimulation of the cardiac tissue slice.

7. The method of claim 1, wherein the cardiac tissue slice is from a human donor heart rejected for transplantation or an explanted human heart.

8. The method of claim 1, further comprising
   (a) treating the cardiac tissue slice with a therapeutic virus comprising a therapeutic gene product,
   (b) seeding cells on the cardiac tissue slice for studying cell therapy,
   (c) performing a gene-editing technique on the cardiac tissue slice for targeted genome editing,
   (d) evaluating the performance of an implantable bioelectronics device built into the tissue culture chamber,
   (e) exposing the cardiac tissue slice to one or more physical fields, or
   (f) a combination thereof.

9. The method of claim 1, wherein the cardiac tissue slice is an atrial or ventricular tissue slice.

10. The method of claim 1, wherein the electrical stimulator comprises a pacing electrode.

11. The method of claim 10, wherein the tissue culture chamber further comprises a bipolar sensing electrode for pseudo ECG recording or an array of unipolar electrodes for measuring electrical conduction.

12. The method of claim 11, wherein the pacing electrode, the bipolar sensing electrode, or each is a platinum-iridium electrode.

13. The method of claim 4, wherein the mechanical loading pole measures contractile force of the cardiac tissue slice.

14. The method of claim 6, wherein the chronic pathological stimulation comprises alpha-adrenergic, beta-adrenergic, or adenosine stimulation.

* * * * *